US006603403B2

(12) United States Patent
Jeutter et al.

(10) Patent No.: US 6,603,403 B2
(45) Date of Patent: Aug. 5, 2003

(54) REMOTE, WETNESS SIGNALING SYSTEM

(75) Inventors: Dean Curtis Jeutter, Grafton, WI (US); Thomas Walter Odorzynski, Green Bay, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/735,349

(22) Filed: Dec. 12, 2000

(65) Prior Publication Data

US 2002/0070868 A1 Jun. 13, 2002

(51) Int. Cl.$^7$ .............................................. G08B 21/00
(52) U.S. Cl. ...................... 340/604; 340/605; 340/361; 340/539; 340/825.34; 340/825.54; 340/941
(58) Field of Search ........................... 340/604, 825.54, 340/941, 361, 539, 825.34, 605

(56) References Cited

U.S. PATENT DOCUMENTS

| 2,108,838 A | 2/1938 | Whitehead ........................ 8/28 |
| 2,127,538 A | 8/1938 | Seiger .......................... 128/138 |
| 2,156,880 A | 5/1939 | Slomon ........................ 116/114 |

(List continued on next page.)

FOREIGN PATENT DOCUMENTS

| CA | 2084803 A1 | * 10/1993 |
| DE | 2 031 104 | * 12/1971 |
| DE | 3437950 A1 | * 4/1985 |

(List continued on next page.)

OTHER PUBLICATIONS

Derwent World Patent Database abstract of Daiki KK (Daik–N): Description of JP10313894 A, "Daily Necessaries Comprising Tissue Paper, Diapers or Toilet Paper."
Derwent World Patent Database abstract of Miles Inc; Bayer Corp.: Description of JP4237500, "Composition Changing Colour in Presence of D–Beta–Hydroxybutyrate."

Derwent World Patent Database abstract of KAO Soap Co. Ltd. (Koas): Description of JP 55036326 A, "Disposable Diaper."

(List continued on next page.)

*Primary Examiner*—Daniel J. Wu
*Assistant Examiner*—Tai T. Nguyen
(74) *Attorney, Agent, or Firm*—Paul Yee; Thomas M. Parker

(57) ABSTRACT

The present invention can provide a monitoring method and system for signaling a predetermined status in an article (20) having a monitored portion (22). The monitoring system includes an interrogator (30) which is located in an operative proximity to the article, and is configured to provide input energy with a predetermined input frequency. A status signaling device (24) is located at the monitored portion (22) of the article. The status signaling device includes a sensor (26) which can indicate a change of state that occurs when the monitored portion (22) of the article (20) changes from a first condition to a different, second condition. A passive transponder (28) is in an operative communication with the sensor (26). In a particular aspect of the invention, the transponder can be an electronic transponder. The transponder (28) can be configured to receive the input energy from the interrogator (30), and can be configured to generate indicator data when the monitored portion (22) is in the second condition. The transponder (28) can be configured to communicate an output energy away from the article (20). The output energy can include at least a portion of the input energy, and the output energy can be configured to carry the indicator data. An output receiver (34) can be configured to electronically acquire the output energy and indicator data from the transponder (28). A detector (36) can be connected to the output receiver (34), and can react to a threshold value of the indicator data. An annunciator (38) can be in communication with the detector (36) and can be configured to announce a presence of the threshold value of the indicator data.

10 Claims, 10 Drawing Sheets

U.S. PATENT DOCUMENTS

| | | | |
|---|---|---|---|
| 2,214,354 A | 9/1940 | Snelling .................... 116/114 |
| 2,249,867 A | 7/1941 | Snelling ..................... 73/335 |
| 2,445,994 A | 7/1948 | Benson et al. ................... 46/1 |
| 2,515,232 A | 7/1950 | Kantrowitz et al. ........ 106/171 |
| 2,577,978 A | 12/1951 | Nicholls et al. ............ 252/408 |
| 2,644,050 A | 6/1953 | Seiger ......................... 200/52 |
| 2,681,032 A | 6/1954 | Shaw ......................... 116/114 |
| 2,698,618 A | 1/1955 | Evenstad ................... 128/138 |
| 2,874,695 A | 2/1959 | Vaniman ................... 128/138 |
| 2,990,253 A | 6/1961 | Smeby ......................... 23/253 |
| 3,001,915 A | 9/1961 | Fonner ................... 195/153.5 |
| 3,004,895 A | 10/1961 | Schwartz ..................... 167/84 |
| 3,006,735 A | 10/1961 | Jordan ......................... 23/230 |
| 3,139,328 A | 6/1964 | Jacob ......................... 23/253 |
| 3,199,095 A | 8/1965 | Ashida ....................... 340/235 |
| 3,212,855 A | 10/1965 | Mast et al. ................... 23/253 |
| 3,266,868 A | 8/1966 | Harvill ........................ 23/253 |
| 3,443,903 A | 5/1969 | Haack et al. ................. 23/230 |
| 3,508,235 A | 4/1970 | Baisden ...................... 340/235 |
| 3,511,608 A | 5/1970 | Anderson .................... 23/253 |
| 3,530,855 A | 9/1970 | Balding ..................... 128/138 |
| 3,634,198 A | 1/1972 | Truhan ...................... 195/160 |
| 3,675,654 A | 7/1972 | Baker et al. ................ 128/187 |
| 3,678,928 A | 7/1972 | Mozes ....................... 128/138 |
| 3,696,357 A | 10/1972 | Kilgore ....................... 340/235 |
| 3,702,610 A | 11/1972 | Sheppard et al. ........... 128/284 |
| 3,731,685 A | 5/1973 | Eidus ......................... 128/284 |
| 3,759,261 A | 9/1973 | Wang ......................... 128/287 |
| 3,778,570 A | 12/1973 | Shuman .................. 200/61.05 |
| 3,802,842 A | 4/1974 | Lange et al. ................. 23/253 |
| 3,818,468 A | 6/1974 | Toth et al. .................. 340/224 |
| 3,850,160 A | 11/1974 | Denson ...................... 128/213 |
| 3,864,676 A | 2/1975 | Macias et al. .............. 340/235 |
| 3,880,590 A | 4/1975 | Ogawa et al. ................ 23/253 |
| 3,897,214 A | 7/1975 | Lange et al. ................. 23/253 |
| 3,898,172 A | 8/1975 | Reif et al. ................... 252/408 |
| 3,918,454 A | 11/1975 | Korodi et al. .............. 128/287 |
| 3,924,607 A | 12/1975 | Bucalo ..................... 128/2 W |
| 3,926,645 A | 12/1975 | Strahl ......................... 106/21 |
| 3,934,575 A | 1/1976 | Bucalo ..................... 128/2 W |
| 3,952,746 A | 4/1976 | Summers ................... 128/287 |
| 3,971,371 A | 7/1976 | Bloom .................... 128/138 A |
| 3,980,437 A | 9/1976 | Kishimoto et al. ........... 23/253 |
| 3,988,209 A | 10/1976 | McDonald ................. 195/139 |
| 4,022,211 A | 5/1977 | Timmons et al. ........... 128/287 |
| 4,038,485 A | 7/1977 | Johnston et al. .......... 23/230 B |
| 4,046,514 A | 9/1977 | Johnston et al. ............. 23/253 |
| 4,059,407 A | 11/1977 | Hochstrasser ................ 23/253 |
| 4,061,468 A | 12/1977 | Lange et al. ................. 23/253 |
| 4,069,817 A | 1/1978 | Fenole et al. .............. 128/38 A |
| 4,097,240 A | 6/1978 | Hirsch ......................... 23/253 |
| 4,106,001 A | 8/1978 | Mahoney ..................... 34/604 |
| 4,147,514 A | 4/1979 | Magers et al. ............ 23/230 B |
| 4,160,008 A | 7/1979 | Fenocketti et al. ........... 422/56 |
| 4,163,449 A | 8/1979 | Regal ..................... 128/138 B |
| 4,184,850 A | 1/1980 | Habenstein ............... 23/230 B |
| 4,191,950 A | 3/1980 | Levin et al. ................ 340/604 |
| 4,192,311 A | 3/1980 | Felfoldi ...................... 128/287 |
| 4,193,068 A | 3/1980 | Ziccardi .................... 340/604 |
| 4,193,766 A | 3/1980 | Daunora et al. .......... 23/230 B |
| 4,205,671 A | 6/1980 | Lassen ................... 128/138 A |
| 4,205,672 A | 6/1980 | Dvorak ................... 128/138 A |
| 4,207,394 A | 6/1980 | Aldridge, Jr. et al. ........ 435/34 |
| 4,212,295 A | 7/1980 | Snyder ................... 128/138 A |
| 4,216,245 A | 8/1980 | Johnson ......................... 427/2 |
| 4,225,669 A | 9/1980 | Melnick et al. ............... 435/29 |
| 4,231,370 A | 11/1980 | Mroz et al. ................. 128/287 |
| 4,250,256 A | 2/1981 | Wielinger et al. ............. 435/32 |
| 4,271,406 A | 6/1981 | Wilson ...................... 340/604 |
| D259,864 S | 7/1981 | Snyder ..................... D10/116 |
| 4,287,153 A | 9/1981 | Towsend ..................... 422/56 |
| 4,288,541 A | 9/1981 | Magers et al. ................ 435/14 |
| 4,303,753 A | 12/1981 | Lam ............................ 435/14 |
| 4,327,731 A | 5/1982 | Powell ....................... 128/287 |
| 4,336,337 A | 6/1982 | Wallis et al. ................ 435/292 |
| 4,347,503 A | 8/1982 | Uyehara .................... 340/604 |
| 4,356,479 A | 10/1982 | Wilson ...................... 340/604 |
| 4,356,818 A | 11/1982 | Macias et al. .......... 128/138 A |
| 4,357,938 A | 11/1982 | Ito et al. .................... 128/287 |
| 4,372,309 A | 2/1983 | Fowler ...................... 128/284 |
| 4,382,062 A | 5/1983 | Kohl ........................... 422/56 |
| 4,438,067 A | 3/1984 | Siddiqi ........................ 422/56 |
| 4,440,724 A | 4/1984 | Tabb et al. ................... 422/56 |
| 4,484,573 A | 11/1984 | Yoo ....................... 128/138 A |
| 4,499,185 A | 2/1985 | Skjold et el. ................. 435/19 |
| 4,507,121 A | 3/1985 | Leung ........................ 664/361 |
| 4,539,559 A | 9/1985 | Kelly et al. ................. 340/573 |
| 4,623,342 A | 11/1986 | Ito et al. ..................... 604/385 |
| 4,635,488 A | 1/1987 | Kremer .................... 73/864.72 |
| 4,640,276 A | 2/1987 | Jing-Sheng ............. 128/138 A |
| 4,647,430 A | 3/1987 | Zweig .......................... 422/56 |
| 4,649,121 A | 3/1987 | Ismail et al. ................. 436/14 |
| 4,653,491 A | 3/1987 | Okada et al. ........... 128/138 A |
| 4,681,576 A | 7/1987 | Colon et al. ................ 604/361 |
| 4,683,209 A | 7/1987 | Ismail et al. ................. 436/14 |
| 4,689,240 A | 8/1987 | Zweig ........................... 427/2 |
| 4,704,108 A | 11/1987 | Okada et al. ............... 604/361 |
| 4,705,513 A | 11/1987 | Sheldon et al. ............. 604/361 |
| 4,717,658 A | 1/1988 | Michaels ..................... 435/19 |
| 4,738,260 A | 4/1988 | Brown ................... 128/138 A |
| 4,738,674 A | 4/1988 | Todd et al. ................. 604/361 |
| 4,743,238 A | 5/1988 | Colon et al. ................ 604/361 |
| 4,749,988 A | 6/1988 | Berman et al. ............. 340/618 |
| 4,754,264 A | 6/1988 | Okada et al. ............... 340/573 |
| 4,760,383 A | 7/1988 | DiLorenzo ................. 340/573 |
| 4,768,023 A | 8/1988 | Xie ............................ 340/573 |
| 4,776,904 A | 10/1988 | Charlton et al. ........... 156/73.1 |
| 4,796,014 A | 1/1989 | Chia ........................... 340/573 |
| 4,800,370 A * | 1/1989 | Vetecnik .................... 340/573 |
| 4,803,158 A | 2/1989 | Shigeta et al. ................ 435/25 |
| 4,810,470 A | 3/1989 | Burkhardt et al. ............ 422/56 |
| 4,834,733 A | 5/1989 | Huntoon et al. ............ 604/361 |
| 4,870,005 A | 9/1989 | Akiyoshi et al. ............... 435/7 |
| 4,895,567 A | 1/1990 | Colon et al. ................ 604/361 |
| 4,909,879 A | 3/1990 | Ball .......................... 156/164 |
| 4,920,046 A | 4/1990 | McFarland et al. ............. 435/7 |
| 4,931,051 A | 6/1990 | Castello .................... 604/361 |
| 4,953,560 A | 9/1990 | Samuels ..................... 128/759 |
| 4,962,025 A | 10/1990 | Moldowan .................. 435/25 |
| 4,973,549 A | 11/1990 | Khanna et al. ............... 435/11 |
| 4,977,906 A | 12/1990 | Di Scipio .................. 128/885 |
| 4,981,653 A | 1/1991 | Marino ........................ 422/56 |
| 5,028,918 A | 7/1991 | Giles et al. ............. 340/825.54 |
| 5,035,691 A | 7/1991 | Zimmel et al. ............. 604/361 |
| 5,036,859 A | 8/1991 | Brown ....................... 128/734 |
| 5,043,704 A | 8/1991 | Blakeney ................... 340/573 |
| 5,066,711 A | 11/1991 | Colon et al. ................ 524/556 |
| 5,071,623 A | 12/1991 | Akutsu ........................ 422/56 |
| 5,074,317 A | 12/1991 | Bondell et al. ............. 128/886 |
| 5,074,853 A | 12/1991 | Bryant ....................... 604/349 |
| 5,075,078 A | 12/1991 | Osikowicz et al. ........... 422/56 |
| 5,077,198 A | 12/1991 | Shih et al. .................... 435/7.9 |
| 5,078,708 A | 1/1992 | Haque ....................... 604/361 |
| 5,081,040 A | 1/1992 | Patel et al. ................... 436/66 |
| 5,089,548 A | 2/1992 | Zimmel et al. ............. 524/272 |
| 5,098,830 A | 3/1992 | Bar-or et al. ................. 435/28 |
| 5,116,729 A | 5/1992 | Ismail et al. ................. 435/14 |
| 5,119,830 A | 6/1992 | Davis ......................... 128/771 |
| 5,121,630 A | 6/1992 | Calvin ........................... 73/73 |
| 5,133,087 A | 7/1992 | Machida et al. ................ 2/168 |
| 5,144,284 A | 9/1992 | Hammett ................... 340/573 |

| Patent | Date | Inventor | Class |
|---|---|---|---|
| 5,167,652 A | 12/1992 | Mueller | 604/385.1 |
| D332,659 S | 1/1993 | Bisaga | D24/124 |
| 5,178,831 A | 1/1993 | Sakota et al. | 422/56 |
| 5,181,905 A | 1/1993 | Flam | 602/41 |
| 5,183,742 A | 2/1993 | Omoto et al. | 435/14 |
| 5,190,863 A | 3/1993 | Magers | 435/25 |
| 5,197,958 A | 3/1993 | Howell | 604/361 |
| 5,211,914 A | 5/1993 | Vogel et al. | 422/56 |
| 5,217,444 A | 6/1993 | Schoenfeld | 604/361 |
| 5,264,830 A | 11/1993 | Kline et al. | 340/604 |
| 5,266,928 A | 11/1993 | Johnson | 340/604 |
| D342,569 S | 12/1993 | Rasfeld | D24/124 |
| D343,232 S | 1/1994 | Lombardi | D24/126 |
| 5,286,624 A | 2/1994 | Terashima et al. | 435/12 |
| 5,291,181 A | 3/1994 | DePonte | 340/604 |
| 5,302,346 A | 4/1994 | Vogel et al. | 422/56 |
| 5,310,646 A | 5/1994 | Whitley | 435/4 |
| 5,327,897 A | 7/1994 | Andresen | 128/764 |
| 5,341,127 A | 8/1994 | Smith | 340/604 |
| 5,342,861 A | 8/1994 | Raykovitz | 523/111 |
| 5,348,855 A | 9/1994 | Dattagupta et al. | 435/6 |
| 5,360,718 A | 11/1994 | Anderson-Mauser | 435/26 |
| 5,371,054 A | 12/1994 | Pluta et al. | 502/62 |
| D354,132 S | 1/1995 | Minor | D24/126 |
| D354,809 S | 1/1995 | Eskey | D24/126 |
| 5,383,867 A | 1/1995 | Klinger | 604/385.1 |
| 5,389,093 A | 2/1995 | Howell | 604/361 |
| 5,392,032 A | 2/1995 | Kline et al. | 340/604 |
| 5,395,358 A | 3/1995 | Lu | 607/361 |
| D358,779 S | 5/1995 | Fabunan | D10/56 |
| 5,416,469 A | 5/1995 | Colling | 340/573 |
| 5,420,014 A | 5/1995 | Cripps et al. | 435/7.32 |
| 5,420,017 A | 5/1995 | Tuompo et al. | 435/29 |
| 5,435,010 A | 7/1995 | May | 2/67 |
| 5,443,987 A | 8/1995 | DeCicco et al. | 435/4 |
| 5,459,452 A | 10/1995 | DePonte | 340/604 |
| 5,463,377 A | 10/1995 | Kronberg | 340/605 |
| 5,468,236 A | 11/1995 | Everhart et al. | 604/361 |
| 5,468,450 A | 11/1995 | Michael | 422/56 |
| 5,469,145 A | 11/1995 | Johnson | 340/604 |
| 5,469,146 A | 11/1995 | Gurler | 340/605 |
| 5,510,245 A | 4/1996 | Magers | 435/26 |
| 5,517,198 A | 5/1996 | McEwan | 342/89 |
| 5,522,809 A | 6/1996 | Larsonneur | 604/361 |
| 5,534,415 A | 7/1996 | Orenga | 435/34 |
| 5,537,095 A | 7/1996 | Dick et al. | 340/605 |
| 5,541,082 A | 7/1996 | Botchner | 435/34 |
| 5,550,536 A * | 8/1996 | Flaxl | 340/825.54 |
| 5,568,128 A | 10/1996 | Nair | 340/604 |
| 5,570,082 A * | 10/1996 | Mahgerefteh et al. | 340/604 |
| D377,452 S | 1/1997 | Boone | D10/40 |
| 5,602,804 A | 2/1997 | Haas | 368/327 |
| 5,647,863 A | 7/1997 | Hammons et al. | 604/378 |
| 5,649,914 A | 7/1997 | Glaug et al. | 604/361 |
| 5,651,869 A | 7/1997 | Yoshioka et al. | 204/403 |
| 5,658,268 A | 8/1997 | Johns et al. | 604/361 |
| 5,681,298 A | 10/1997 | Brunner et al. | 604/361 |
| 5,690,624 A | 11/1997 | Sasaki et al. | 604/361 |
| 5,702,376 A | 12/1997 | Glaug et al. | 604/361 |
| 5,705,160 A | 1/1998 | Bruce et al. | 424/195.1 |
| 5,709,222 A | 1/1998 | Davallou | 128/885 |
| 5,719,034 A | 2/1998 | Kiser et al. | 435/14 |
| 5,728,350 A | 3/1998 | Kinoshita et al. | 422/61 |
| 5,760,694 A | 6/1998 | Nissim et al. | 340/604 |
| 5,762,871 A | 6/1998 | Neyer | 422/57 |
| 5,766,212 A | 6/1998 | Jitoe et al. | 604/361 |
| 5,770,441 A | 6/1998 | Lipton | 435/289.1 |
| 5,776,694 A | 7/1998 | Sheiness et al. | 435/6 |
| 5,780,385 A | 7/1998 | Santioemmo et al. | 502/401 |
| 5,796,345 A | 8/1998 | Leventis et al. | 340/604 |
| 5,797,892 A | 8/1998 | Glaug et al. | 604/361 |
| 5,804,179 A | 9/1998 | Bruce et al. | 424/93.45 |
| 5,808,554 A | 9/1998 | Shuminov | 340/604 |
| 5,817,076 A | 10/1998 | Fard | 604/361 |
| 5,823,953 A | 10/1998 | Roskin et al. | 600/367 |
| 5,838,240 A | 11/1998 | Johnson | 340/604 |
| 5,843,691 A | 12/1998 | Douglas et al. | 435/14 |
| 5,858,515 A | 1/1999 | Stokes et al. | 428/195 |
| 5,858,697 A | 1/1999 | Groner et al. | 435/34 |
| 5,868,723 A | 2/1999 | Al-Sabah | 604/361 |
| 5,876,389 A | 3/1999 | Bouchard et al. | 604/385.1 |
| 5,876,952 A | 3/1999 | Shieh | 435/14 |
| 5,882,600 A | 3/1999 | Davis | 422/102 |
| 5,902,296 A | 5/1999 | Fluyeras | 604/361 |
| 5,903,222 A | 5/1999 | Kawarizadeh et al. | 340/604 |
| 5,904,671 A | 5/1999 | Navot et al. | 604/361 |
| 5,908,411 A * | 6/1999 | Matsunari | 604/361 |
| 5,947,943 A | 9/1999 | Lee | 604/361 |
| 5,948,695 A | 9/1999 | Douglas et al. | 436/518 |
| 5,959,535 A | 9/1999 | Remsburg | 340/604 |
| 5,961,470 A | 10/1999 | Wagner et al. | 600/532 |
| 5,976,469 A | 11/1999 | Davis | 422/102 |
| 5,989,917 A | 11/1999 | McAleer et al. | 436/46 |
| 5,994,149 A | 11/1999 | Robinson et al. | 436/518 |
| 6,019,734 A | 2/2000 | Parkinson | 600/572 |
| 6,040,195 A | 3/2000 | Carroll et al. | 436/514 |
| D423,098 S | 4/2000 | Stancyk, Jr. | D24/126 |
| 6,048,735 A | 4/2000 | Hessel et al. | 436/518 |
| D423,955 S | 5/2000 | Mohammed et al. | D10/56 |
| 6,080,539 A | 6/2000 | Zeytinoglu et al. | 435/5 |
| 6,093,869 A | 7/2000 | Roe et al. | 604/361 |
| 6,097,297 A | 8/2000 | Fard | 340/604 |
| 6,101,366 A | 8/2000 | Castillo | 434/308 |
| 6,106,461 A | 8/2000 | Roskin et al. | 436/165 |
| 6,150,178 A | 11/2000 | Cesarczyk et al. | |
| 6,165,796 A | 12/2000 | Bell | 436/74 |
| 6,171,868 B1 | 1/2001 | Rolon et al. | 436/174 |
| 6,174,293 B1 | 1/2001 | Buck et al. | 600/572 |
| 6,174,664 B1 | 1/2001 | Heine | 435/4 |
| 6,203,496 B1 | 3/2001 | Gael et al. | 600/362 |

FOREIGN PATENT DOCUMENTS

| | | | |
|---|---|---|---|
| DE | 3516402 A1 | * | 11/1986 |
| DE | 3608114 A1 | * | 9/1987 |
| DE | 3810473 A1 | * | 10/1989 |
| DE | 4014213 A1 | * | 11/1991 |
| DE | 4403437 A1 | * | 8/1995 |
| EP | 0 402 023 A1 | * | 12/1990 |
| EP | 0 407 800 A2 | * | 1/1991 |
| EP | 0 288 621 B1 | * | 3/1993 |
| EP | 0 310 862 B1 | * | 4/1993 |
| EP | 0 290 610 B1 | * | 8/1994 |
| EP | 0 471 728 B1 | * | 11/1995 |
| EP | 0 463 524 B1 | * | 3/1996 |
| EP | 0 735 369 A1 | * | 10/1996 |
| EP | 0 759 555 A2 | * | 2/1997 |
| EP | 0 705 089 B1 | * | 5/1997 |
| EP | 0 815 821 A2 | * | 1/1998 |
| EP | 0 733 208 B1 | * | 4/1998 |
| EP | 0 850 631 A1 | * | 7/1998 |
| EP | 0 852 336 A1 | * | 7/1998 |
| EP | 0 904 758 A2 | * | 3/1999 |
| EP | 0 605 394 B1 | * | 4/1999 |
| EP | 0 911 000 A1 | * | 4/1999 |
| EP | 0 925 769 A2 | * | 6/1999 |
| EP | 0 997 125 A1 | | 5/2000 |
| FR | 1355018 | | 2/1964 |
| FR | 2 486 112 | | 1/1982 |
| FR | 2 541 872 | | 9/1984 |
| FR | 2 559 037 | | 8/1985 |
| GB | 2 022 423 A | | 12/1979 |
| GB | 2 250 121 A | | 5/1992 |

| | | | | | | |
|---|---|---|---|---|---|---|
| GB | 2 321 990 A | 8/1998 | | WO | WO 00/00138 A1 | 1/2000 |
| GB | 2 237 954 A | 1/1999 | | WO | WO 00/00144 A1 | 1/2000 |
| GB | 2 348 137 A | 9/2000 | | WO | WO 00/00148 A1 | 1/2000 |
| JP | 58-174601 | 10/1983 | | WO | WO 00/00150 A1 | 1/2000 |
| JP | 3058416 | 6/1991 | | WO | WO 00/00151 A1 | 1/2000 |
| JP | 8024292 | 1/1996 | | WO | WO 00/00233 A1 | 1/2000 |
| JP | 10-151154 | 6/1998 | | WO | WO 00/15169 A1 | 3/2000 |
| JP | 11004852 | 1/1999 | | WO | WO 00/24438 A1 | 5/2000 |
| JP | 3060006 | 7/1999 | | WO | WO 00/25836 A1 | 5/2000 |
| JP | 3062395 | 10/1999 | | WO | WO 00/39579 A1 | 7/2000 |
| WO | WO 85/01747 A1 | 4/1985 | | WO | WO 00/52472 A1 | 9/2000 |
| WO | WO 92/17768 A1 | 10/1992 | | WO | WO 00/53798 A1 | 9/2000 |
| WO | WO 94/24557 A1 | 10/1994 | | WO | WO 00/65083 A1 | 11/2000 |
| WO | WO 95/15739 A1 | 6/1995 | | WO | WO 00/65084 A1 | 11/2000 |
| WO | WO 96/25904 A1 | 8/1996 | | WO | WO 00/65096 A1 | 11/2000 |
| WO | WO 96/28570 A1 | 9/1996 | | WO | WO 00/65347 A1 | 11/2000 |
| WO | WO 97/06428 A1 | 2/1997 | | WO | WO 00/65348 A1 | 11/2000 |
| WO | WO 97/14127 A1 | 4/1997 | | WO | WO 01/00117 A2 | 1/2001 |
| WO | WO 98/04225 A1 | 2/1998 | | WO | WO 01/16576 A1 | 3/2001 |
| WO | WO 98/12997 A1 | 4/1998 | | | | |
| WO | WO 98/30179 A1 | 7/1998 | | | | |
| WO | WO 98/42481 A1 | 10/1998 | | | | |
| WO | WO 99/16401 A1 | 4/1999 | | | | |
| WO | WO 99/17692 A1 | 4/1999 | | | | |
| WO | WO 99/18232 A1 | 4/1999 | | | | |
| WO | WO 99/20216 A1 | 4/1999 | | | | |
| WO | WO 99/23985 A1 | 5/1999 | | | | |
| WO | WO 99/33037 A1 | 7/1999 | | | | |
| WO | WO 99/51179 A1 | 10/1999 | | | | |
| WO | WO 99/63497 A1 | 12/1999 | | | | |
| WO | WO 00/00082 A1 | 1/2000 | | | | |
| WO | WO 00/00137 A1 | 1/2000 | | | | |

OTHER PUBLICATIONS

Abstract of Benkert,L.; Description of DE2702388 A; "Wet Nappy Monitoring System".

F.E. Terman; *Radio Engineers Handbook*; first edition; McGraw Hill Book Company, Inc., New York; 1943, e.g. pp. 67–73.

Patent Cooperation Treaty Search Report from the International Search Authority, International Application No. PCT/US 01/47600 dated Mar. 26, 2002.

* cited by examiner

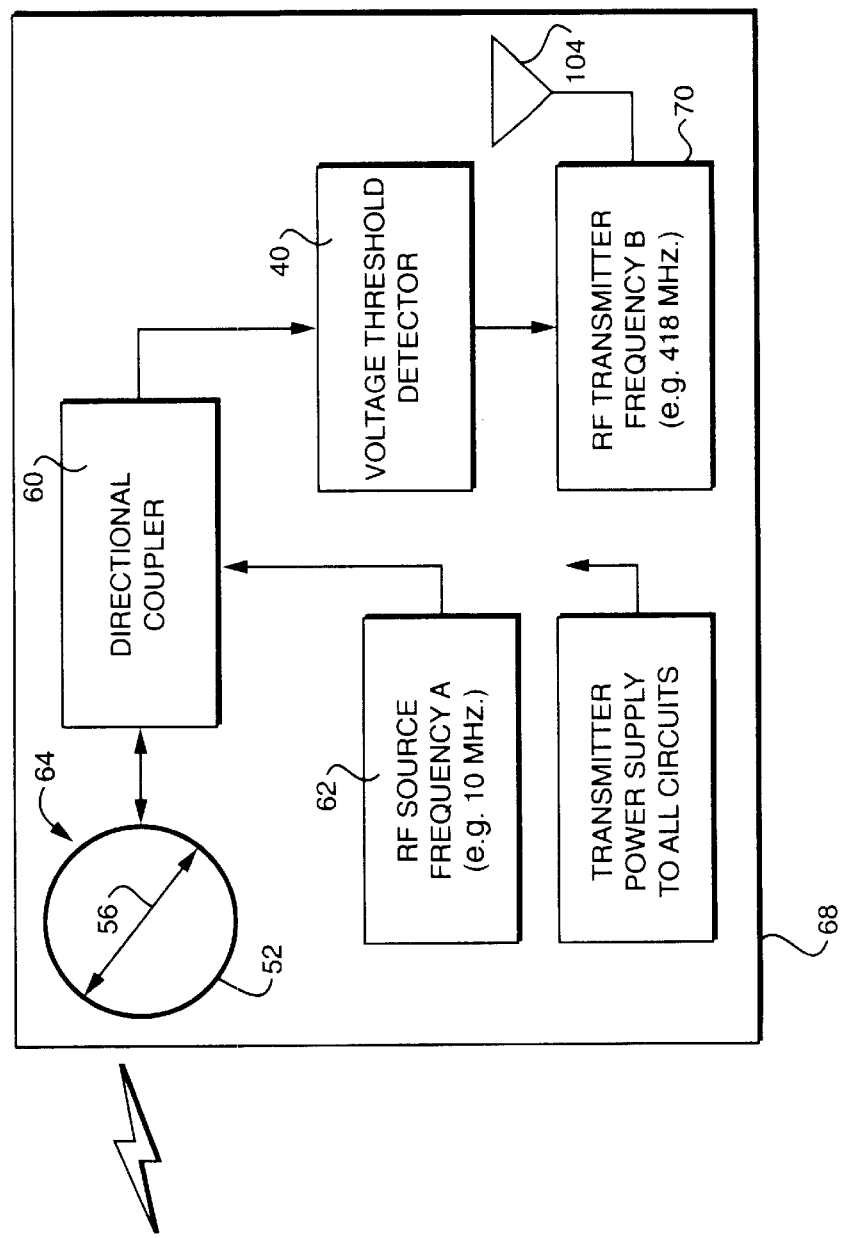
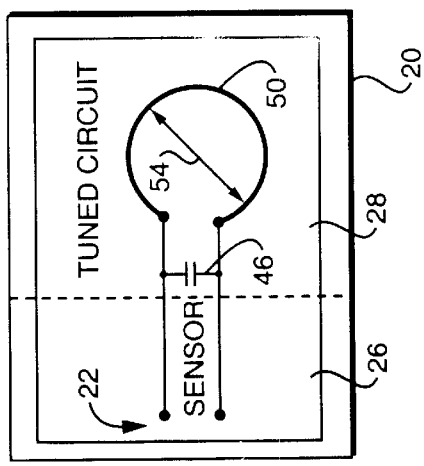
FIG. 5A
FIG. 5

REMOTE, WETNESS SIGNALING SYSTEM

FIELD OF THE INVENTION

The present invention relates to a status signaling device or system which can be employed with a selected article. In particular aspects, the present invention can provide a wetness signaling device or system, and the device or system may be employed with absorbent articles, such as gowns, diapers, children's training pants, feminine care products, incontinence garments and the like.

BACKGROUND OF THE INVENTION

Conventional signaling systems have been incorporated into conventional articles to alert a care-giver to changes in status of the articles. For example, conventional signaling systems have been incorporated into disposable absorbent articles, such as diapers and incontinence garments. The absorbent articles have typically employed absorbent pads or other absorbent structures sandwiched between a backsheet layer and a liquid permeable liner layer. The absorbent structures have incorporated superabsorbent materials combined with fibrous matrices composed of natural and synthetic fibers. For example, the absorbents structures have included superabsorbent particles mixed with cellulosic, woodpulp fluff.

The signaling systems have typically been employed to alert the user of a change in wetness of the absorbent structure. Some conventional signaling devices have included a mechanism that undergoes a change in color or other change in visual appearance when the absorbent has become wetted. For example, absorbent articles have employed decorative patterns or graphic that become visible or fade away when the article has become wetted. Other conventional devices have incorporated a frangible component that can break to signal a wet condition of the absorbent. Still other conventional devices have employed active, electronic systems which have been incorporated into the selected absorbent article. The electronic devices have included power supplies, and have employed powered audio or visual displays, such as buzzers or lights. Particular arrangements have also employed radio transmitters to send the wetness alert to a remote radio receiver.

Conventional devices and systems, such as those described above, have not been sufficiently satisfactory. Systems that have employed color-change or other visual-change mechanisms are easily obscured by overlying layers, such as blankets or layers of clothing. When such systems are arranged to be readily visible, the systems have been indiscriminate and indiscrete, and have undesirably provided the wetness information to persons other than the care-giver. Systems that have employed a frangible component have had similar shortcomings. Systems that have employed a power source positioned internal to the associated article have been undesirable to consumers. As a result, there has been a continued need for improved techniques and systems for signaling a change in the internal status of a selected article.

BRIEF DESCRIPTION OF THE INVENTION

The present invention can provide a monitoring method and system for signaling a predetermined status in an article having a monitored portion. The monitoring system includes an interrogator which can be located in an operative proximity to the article, and can be configured to provide input energy with a predetermined input frequency. A status signaling device is located at the monitored portion of the article. The status signaling device includes a sensor which can indicate a change of state that occurs when the monitored portion of the article changes from a first condition to a different, second condition. In a particular aspect, a passive transponder can be arranged in an operative communication with the sensor. In another aspect, the transponder can be configured to receive the input energy from the interrogator, and can be configured to generate indicator data when the monitored portion is in the second condition. The transponder can be configured to communicate an output energy away from the article. In a further aspect, the output energy can include at least a portion of the input energy, and the output energy can be configured to carry the indicator data. In an additional aspect, an output receiver can be configured to electronically acquire the output energy and indicator data from the transponder. In still another aspect, a detector can be connected to the output receiver, and can react to a threshold value of the indicator data. An annunciator can be arranged in communication with the detector and can be configured to announce a presence of the threshold value of the indicator data.

The incorporation of the various aspects can provide an improved article which incorporates a distinctive status signaling technique and apparatus. The status signaling apparatus can be discrete, and can provide the wetness information to the care-giver without also providing the information to other casual observers. The technique and apparatus of the invention can avoid the use of a power source positioned internal to the associated article, and can be less susceptible to the generation of undesired, stray electrical currents.

BRIEF DESCRIPTION OF THE DRAWINGS

The present invention will be more fully understood and further advantages will become apparent when reference is made to the following detailed description of the invention and the drawings, in which:

FIG. 5 representatively shows a schematic block diagram of an electronic sensor and passive transponder that can be employed with the present invention;

FIG. 5A representatively shows a schematic block diagram of package module that can be employed with the present invention, and can include the interrogator and associated annunciator, with or without a remote-paging transmitter;

FIG. 6 (i.e.

DETAILED DESCRIPTION OF THE INVENTION

Figure 1:
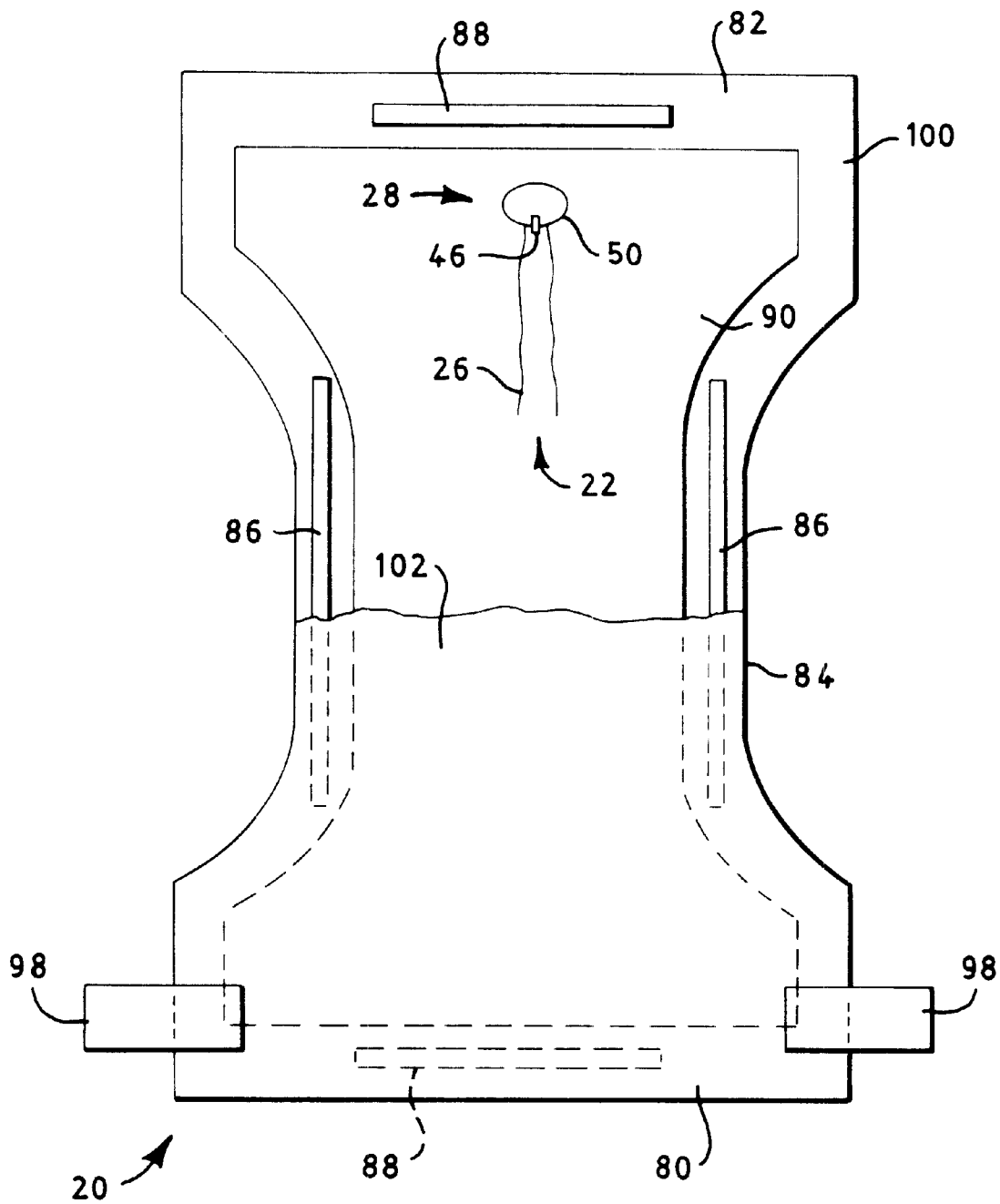
FIG. 1 representatively shows a partially cut-away, top plan view of an outward side of an article which incorporates an apparatus and method of the invention.

The various aspects and embodiments of the invention will be described in the context of a disposable absorbent article, such as a disposable diaper. It is, however, readily apparent that the present invention could also be employed with other articles, such as caps, gowns, shoe covers, feminine care articles, children's training pants, incontinence garments, and packaging articles. Typically, the disposable articles are intended for limited use and are not intended to be laundered or otherwise cleaned for reuse. A disposable diaper, for example, is discarded after it has become soiled by the wearer.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

With reference to FIGS. 1 through 3A, the present invention can provide a distinctive article 20 having a monitored portion 22, and a status signaling device 24 for communicating a change in status of the monitored portion. In a desired aspect, the change in status can occur internal to the article. The status signaling device includes a sensor 26 which can indicate a change of state that occurs when the monitored portion 22 of the article 20 changes from a first condition to a different, second condition. In a particular aspect of the invention, a passive electronic transponder 28 can be cooperatively connected with the sensor 26. In other aspects, the transponder 28 can be configured to receive electromagnetic input energy which has been provided to the transponder at a predetermined input frequency, and the transponder 28 can be configured to respond with operative indicator data when the monitored portion 22 is in the second condition.

A process aspect of the invention can provide a method for communicating a change in status of a monitored portion 22 of an article 20. The method includes a positioning of a status signaling mechanism 24 in the article 20. The status signaling mechanism includes a sensor 26 which can indicate a change of state that occurs when the monitored portion 22 of the article 20 changes from a first condition to a different, second condition. In a particular aspect of the method, a passive electronic transponder 28 can be provided to operatively cooperate with the sensor 26. In other aspects, the transponder 28 can be configured to receive electromagnetic input energy which has been provided to the transponder at a predetermined input frequency. The transponder 28 can be configured to respond with operative indicator data when the monitored portion 22 of the article is in the second condition.

The present invention can also provide a monitoring method and apparatus for signaling a predetermined status in an article 20 having a monitored portion 22. The monitoring technique or system includes an interrogator 30 which can be located in an operative proximity to the article, and can be configured to provide input energy with a predetermined input frequency. A status signaling device 24 is located at the monitored portion 22 of the article. The status signaling device includes a sensor 26 which can indicate a change of state that occurs when the monitored portion 22 of the article 20 changes from a first condition to a different, second condition. A passive transponder 28 is in an operative communication with the sensor 26. In a particular aspect of the invention, the transponder can be an electronic transponder. The transponder 28 can be configured to receive the input energy from the interrogator 30, and can be configured to generate indicator data when the monitored portion 22 is in the second condition. The transponder 28 can be configured to communicate an output energy away from the article 20. The output energy includes at least a portion of the input energy, and the output energy can be configured to carry the indicator data. An output receiver 34 can be configured to electronically acquire the output energy and indicator data from the transponder 28. A detector 36 can be connected to the output receiver 34, and can react to a threshold value of the indicator data. An annunciator 38 can be in communication with the detector 36 and can be configured to announce a presence of the threshold value of the indicator data.

In particular aspects, the invention can include a transmission of high frequency energy from a transmitting antenna coil to a receiving coil embedded in a non-metallic substrate. In particular arrangements the invention can provide a device for indicating changes in the resistance appearing between electrodes that are embedded in the substrate. A feature of the invention can include an indicating of a resistance change with the use of a wireless link across a non-metallic substrate. A desired configuration can, for example, indicate a wetness condition produced by the introduction or other revealed presence of an electrically conductive material, such as urine or other conductive liquid. Another feature can include a detection of a resistance change by means of measuring the amount of reflected power from an embedded tuned circuit into a coupled tuned circuit. A further feature can include a wireless sensing of the wetness of a non-metallic substrate material that results in a resistance change experienced by embedded electrodes that can be detected by measuring the amount of reflected power from a coupled, embedded tuned circuit.. Still another feature of the invention can provide a system that ultimately signals a resistance change by wireless means to a remotely located monitor.

The aspects or features of the invention, alone and in combination, can provide various advantages. Such advantages may, for example, include a non-intrusive monitoring of electrical impedance or electrical conductivity changes employing a wireless approach. The method and apparatus can provide a wireless sensing of the electrical impedance and wetness status through a non-metallic substrate, and can provide a wireless signaling of the change in electrical impedance and wetness status. In a particular arrangement, the impedance change can include a change in electrical resistance. The electrical impedance change in a monitored substrate can be sensed by measuring changes in power reflected from the embedded part into an external, coupled, tuned circuit. The method and apparatus of the invention can have no direct electrical connection between its external sensing electronics and its embedded portion. As a result, there can be no degradation of any electrical contacts that might otherwise interconnect such components. Any actively powered circuits are electrically isolated from the inside of the article. As a result, there can be substantially no risk of stray, electrical leakage currents. The method and apparatus of the invention can provide a distinctive magnetic coupling between its embedded part and a separate, external sensing part. The embedded part can be readily incorporated into a selected garment or other non-metallic substrate, and the embedded part may comprise a simple, two component tuned circuit. Additionally, the method and apparatus of the invention can include a portable, external sensing mechanism, and alert signal transmitting mechanism. A wireless alert signal can be sent to a remotely located monitor.

Figure 2:
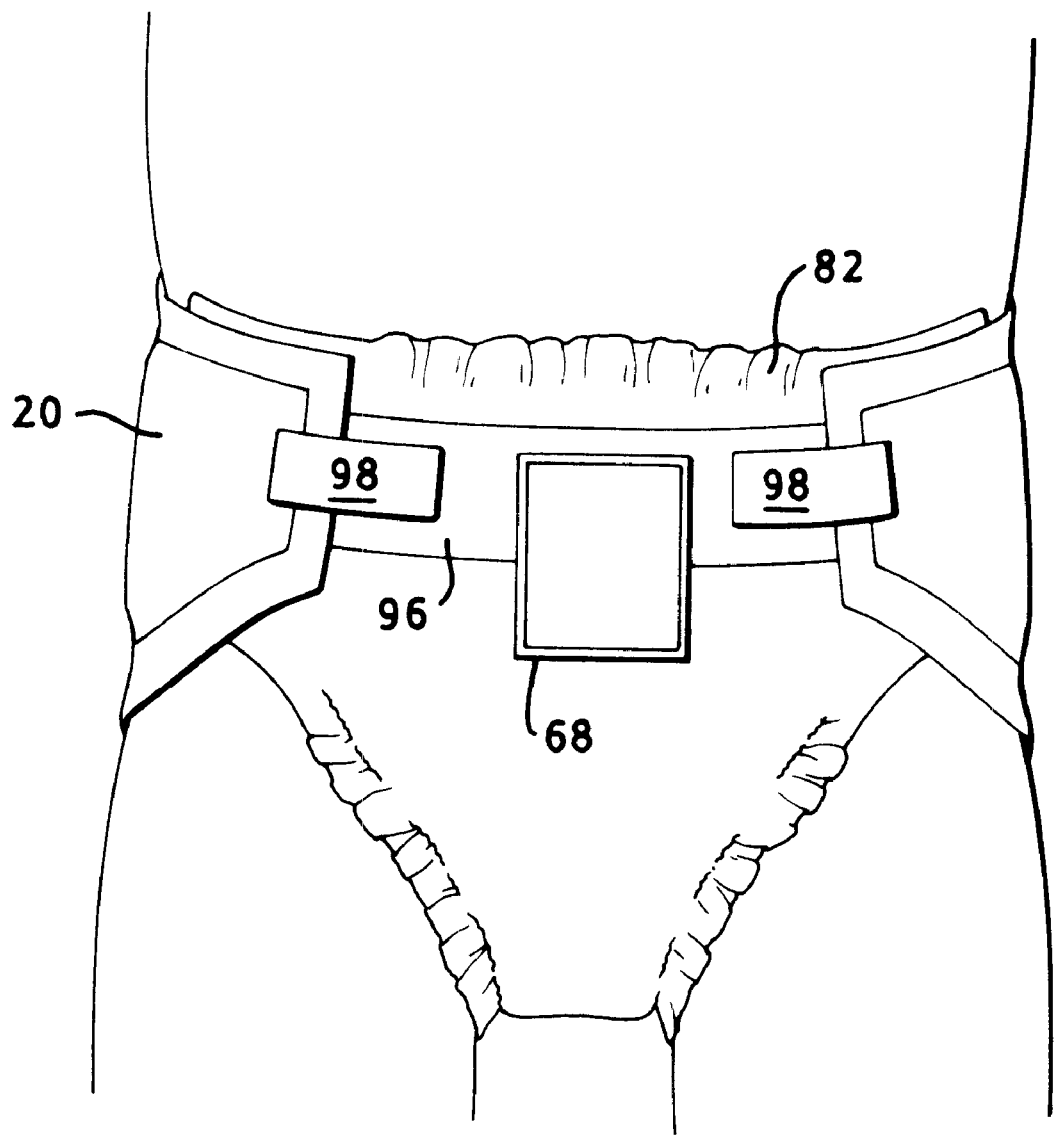
FIG. 2 representatively shows a front view of the outward side of an article which has been placed on a wearer and incorporates an apparatus and method system of the invention.

With reference to FIGS. 1 and 2, the selected article, such as the representatively shown diaper article 20, can include a backsheet layer 102, a liquid-permeable topsheet layer 100, and an absorbent body 90 sandwiched between the backsheet layer 102 and topsheet layer 100. In particular aspects, the backsheet layer can be substantially liquid-impermeable. In other aspects the backsheet layer can be vapor permeable or "breathable".

In desired configurations, the article can provide a first waistband portion, such as the shown rear or back waistband portion 80, and a second waistband portion, such as the shown front waistband portion 82. The article can additionally have an intermediate or crotch portion 84 which interconnects between the first and second waistband portions 80 and 82, respectively. A system of elastomeric gathering or gasketing members, such as a system including leg elastics 86 and/or waist elastics 88, may be employed to help improve fit and reduce leakage. An operative fastening system, such as provided by the shown system having fasteners 98, may be employed to interconnect the first waistband portion 80 with the second waistband portion 82 to hold the article on a wearer. The fastening system can be operatively configured to join the first, back waistband portion 80 in an overlapping relation with the second, front waistband portion 82 in a back-to-front arrangement to thereby encircle the wearer's body and hold the diaper secure on the wearer during use. Optionally, the fastening system can employ fasteners 98 which are configured to join the front waistband portion 82 in an overlapping relation with the back waistband portion 80 in a front-to-back arrangement to secure the diaper. In such optional arrangements, the front waistband region may be identified as the first waistband portion 80 and the rear waistband region may be identified as the second waistband portion 82. It should be readily apparent that fully configured articles, such as children's training pants, feminine care panties, incontinence garments, and other fully constructed, 3-dimensional articles may not include fasteners.

FIGS. 1 and 2 show typical views of the representative disposable diaper 20. In FIG. 1, portions of the structure are partially cut away to more clearly show the interior construction of the diaper article, and the bodyside surface of the diaper which contacts the wearer is facing away from the viewer. The outer edges of the diaper define a periphery with longitudinally extending side edge margins and laterally extending end edge margins. The side edges define leg openings for the diaper, and optionally, are curvilinear and contoured. The end edges are shown as straight, but optionally, may be curvilinear.

With regard to the designated surfaces of the article, the various inward or bodyside surfaces are configured to face toward the body of the wearer when the article is placed about the wearer. The designated outward surfaces of the article are configured to face away from the wearer's body when the article is placed about the wearer.

The various components of the article may be assembled together by employing various conventional attachment techniques and mechanisms, such as adhesives, sonic bonds, thermal bonds, welds, stitching, snaps, pins, rivets, buttons and the like, as well as combinations thereof. The attachment mechanisms may be arranged in any operative pattern or configuration.

The topsheet 100, backsheet 102, absorbent body 90, and other components of the article are connected or otherwise associated together in an operable manner. The various components can, for example, be operatively joined to each other with suitable attachment mechanisms (not shown) such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be employed to suitably interconnect, assemble and/or affix together the various component parts of the article.

The absorbent body 90 provides an absorbent retention portion, such as provided by the representatively shown absorbent pad composed of selected hydrophilic fibers and high-absorbency particles. The retention portion is configured to hold and store absorbed liquids and other waste materials. The absorbent body can be positioned and sandwiched between the topsheet 100 and backsheet 102 to form the diaper 20 or other absorbent article. The absorbent body has a construction which is generally compressible, conformable, non-irritating to the wearer's skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 90. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

The absorbent body structure 90 can comprise a matrix of hydrophilic fibers, such as a web of cellulosic fluff, mixed with particles of high-absorbency material. In particular arrangements, absorbent body 90 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed.

To improve the containment of the high-absorbency material, absorbent body structure 90 can include an overwrap or wrap sheet, which can be placed immediately adjacent and around the absorbent body. The wrap sheet may be bonded to the absorbent structure and to the various other components of the article. The wrap sheet may be a layer of absorbent material or substantially non-absorbent material, which covers the major bodyside and/or outerside surfaces of the absorbent body. The wrap sheet may enclose substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body.

For example, the complete wrap sheet, or at least the bodyside layer of the wrap sheet, may comprise a meltblown web composed of meltblown fibers, such as meltblown polypropylene fibers. Another example of absorbent wrap may comprise a low porosity cellulosic web, such as a tissue composed of an approximately 50/50 blend of hardwood/softwood fibers.

In the various aspects and configurations of the invention, the fastening mechanism between the selected first fastener component and the selected, second fastener component may be adhesive, cohesive, mechanical or combinations thereof. In the context of the present invention, a mechanical fastening system is a system which includes cooperating, first and second components which mechanically interengage to provide a desired securement.

Desirably, the first and second fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components.

As shown in the illustrated arrangements, for example, the mechanical fastening system may be a hook-and-loop type of fastening system. Such fastening systems typically include attachment members having the form of a "hook" or hook-like, male component, and include a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single-prong hook configuration, a multiple-prong hook configuration or by a generally continuous, expanded-head configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

A configuration which employs a selectively releasable, interengaging mechanical fastening system can, for example, locate the first fastener component on at least the appointed mating or securing surface of the fastener tab 98, and can locate the cooperating, second fastener component on the appointed engagement surface of the appointed landing member 96. For example, with the representatively shown hook-and-loop fastener, the fastening component which is attached to the appointed mating or securing surface of the fastener tab 98 may include a hook type of mechanical engagement element, and the complementary fastening component, which is operably joined and attached to the appointed landing zone member 96 can include a loop type of fastening element.

It should also be readily apparent that, in the various configurations of the invention, the relative positions and/or materials of the first fastening component and its cooperating, complementary second fastening component can be transposed. Accordingly, the fastening component, which is attached to the appointed mating surface of the fastener tabs 98, may include the loop type of mechanical fastening element; and the complementary, second fastening component, which is operatively joined and attached to the appointed landing zone member, can include the hook type of attachment members.

For the various configurations of the invention, an example of a suitable attachment hook member is a micro-hook member provided in a material which is distributed under the designation VELCRO HTH 829, and is available from VELCRO U.S.A., Inc., a business having offices in Manchester, N.H. The micro-hook material has attachment members in the shape of angled, prong-type hook members. The hook members can be configured with a hook height which is within the range of about 0.030–0.063 cm (about 0.012–0.025 inch); and a hook width which is within the range of about 0.007 to 0.022 cm (about 0.003 to 0.009 inch). The hook elements are molded onto a base layer substrate having a thickness of about 0.0076–0.008 cm (about 0.003–0.0035 inch). Another suitable type of attachment hook member can be found on a 3M CS200 material available from the Minnesota Mining and Manufacturing (3M) Company, a business having offices in St. Paul, Minn. Other suitable hook materials are available from various vendors, such as VELCRO U.S.A., Inc. and the 3M Company.

In the various configurations of the invention, the loop material can be provided by a nonwoven, woven or knit fabric, as well as combinations thereof. For example, a suitable loop material fabric can be composed of a 2 bar, warp knit fabric of the type available from Guilford Mills, Inc., Greensboro, N.C. under the trade designation #34285, as well as other types of knit fabrics. Suitable loop materials are also available from the 3M Company, which has distributed a nylon woven loop under their SCOTCHMATE brand. The 3M Company has also distributed a liner-less loop web with adhesive on the backside of the web, and 3M knitted loop tape.

The loop material may also include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515 entitled PATTERN-UNBONDED NONWOVEN WEB AND PROCESS FOR MAKING THE SAME, by T. J. Stokes et al., which issued Jan. 12, 1999 (attorney docket No. 12,232); the entire disclosure of which is incorporated herein by reference in a manner that is consistent herewith.

The loop material employed in the various configurations of the invention need not be limited to a discrete or isolated patch on the outward surface of the article. Instead, the loop material can be provided by a substantially continuous, outer fibrous layer which is assembled, integrated or otherwise joined to extend over a predetermined surface area of the desired article. For example, the outer fibrous layer may be arranged to extend over substantially the total exposed surface area of a cloth-like outer cover employed with the article.

In the various configurations of the invention, the engagement force between the selected first fastener component and its appointed and cooperating second fastener component should be large enough and durable enough to provide an adequate securement of the article on the wearer during use.

Figure 3:
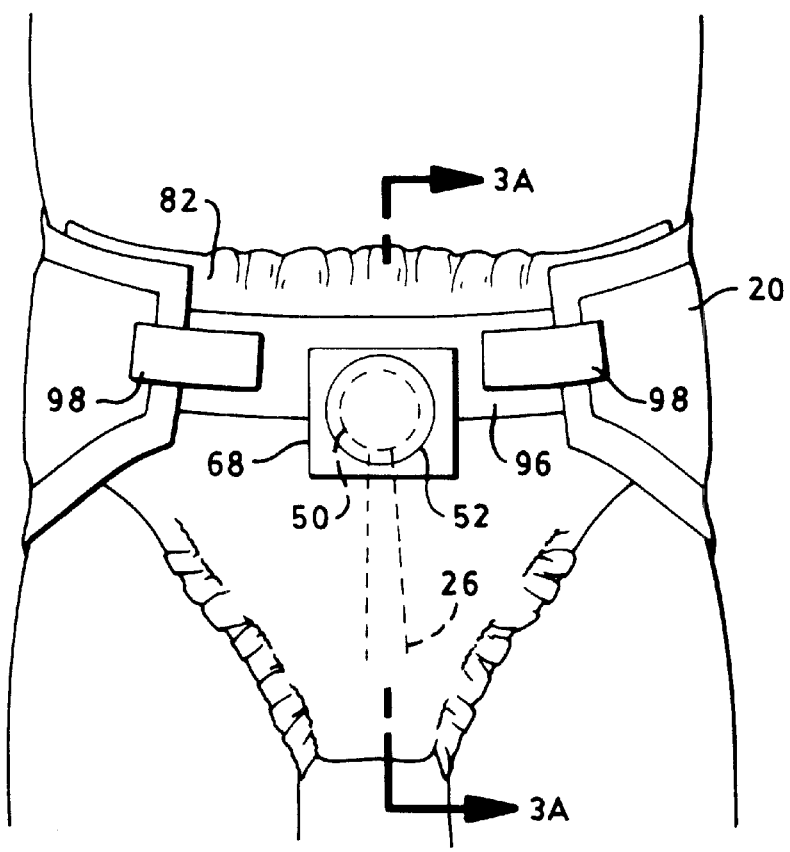
FIG. 3 representatively shows a schematic front view of the outward side of the article illustrated in FIG. 2, wherein a portion of a package module has been partially cut away to illustrate a relative positioning of a transponder coil and an interrogator coil mounted on the article.
Figure 3A:
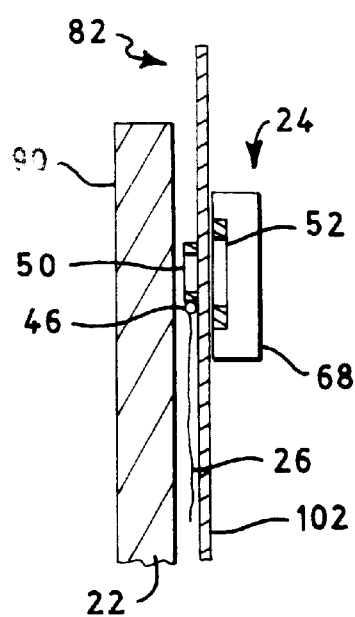
FIG. 3A representatively shows a partial, schematic, cross-sectional view taken along section 3A—3A of FIG. 3.

With reference to FIGS. 1, 3 and 3A, the monitored portion 22 can be any desired region of the selected article. For example, the appointed monitored portion 22 can be a predetermined region of the absorbent body 90 in the article. In desired arrangements, the monitored portion of the absorbent body can be a section which is appointed to absorb and retain urine or other bodily fluids.

The monitored status can be any desired characteristic of the monitored portion 22. For example, the monitored status may be a level of moisture, a level of light, sound, heat or the like, as well as combinations thereof. In the example of the representatively shown article, the monitored characteristic can be the wetness of the monitored portion of the absorbent.

The sensor 26 can indicate the desired change of state by employing various operative techniques. The sensor may, for example, include a chemical sensor, a mechanical sensor, an electronic sensor or the like, as well as combinations thereof. The chemical sensor can be configured to respond by undergoing a chemical reaction, a change in color or other change in its chemistry. The mechanical sensor may dissolve, break, physically disperse or undergo some other physical transformation. The electronic sensor can include any type of electrical or electronic circuit with passive or active components. The passive components can include resistors, capacitors, inductors, thyristors, diodes, interconnecting wires, antenna and the like, as well as combinations thereof. Active components can include transistors, solar cells, batteries, integrated circuits, transistorized circuits and the like, as well as combinations thereof.

In the example of the representatively shown arrangement, the sensor 26 can be an electronic sensor. More particularly, the sensor 26 can be configured to indicate the change of state by providing a change of electronic impedance that occurs when the monitored portion 22 of the absorbent body changes from the first condition to the second condition. In desired arrangements, the first condition can be a substantially dry condition, and the second condition can be a wetted condition. Accordingly, the passive transponder 28 can be configured to respond with the selected indicator data when the absorbent body 90 is, for example, in the wetted, second condition. The status signaling device can thereby provide a wetness signaling device.

In a particular aspect, the sensor 26 can provide a changeable resistive impedance. In another aspect, the sensor 26 can provide a changeable, capacitive impedance. The impedance of the sensor 26 can be configured to change when the monitored portion 22 of the article changes from its first condition to its second condition. In more particular arrangements, the impedance of the sensor 26 can change when the monitored portion 22 of the article changes from its first substantially dry condition to its wetted second condition.

An advantageous feature of the invention can include the incorporation of the passive transponder 28. The transponder 28 is passive to the extent that it does not include a conventional power supply, such as a battery, solar cell, wound spring, electrical generator or other conventional mechanism which is ordinarily considered to be a power source. Accordingly, the passive transponder can include a passive electronic device, a passive mechanical device, a passive optical device, a passive chemical device or the like, as well as combinations thereof.

In desired arrangements, the transponder 28 is a passive electronic transponder which includes an operative coupler configured to communicate the indicator data away from the article 20. The coupler may be mechanical, chemical, radiant, optical, electronic or the like, as well as combinations thereof. In the example of the representatively shown arrangement, the method and apparatus of the invention can include an electronic coupler. The method and apparatus may employ a capacitive coupler, an inductive coupler, a light coupler, a heat coupler, a sound coupler, a reflector or the like, as well as combinations thereof. In the representatively shown example, the method and apparatus include an inductive coupler.

An interrogator 30 can be configured to provide the desired input energy with the predetermined input frequency. The interrogator can, for example, be configured to provide the input energy at any operative frequency. In desired aspects, the input frequency can be an operative frequency in the electromagnetic spectrum. The frequency of the input energy may, for example, be an audio frequency or other sonic frequency, a radio-frequency, a microwave frequency, an infrared frequency, an optically visible frequency, an ultraviolet frequency or other higher or lower frequencies, as well as combinations thereof. The interrogator 30 may be a component that is integrally assembled into the article at an operative location. Alternatively, the interrogator may be provided by a component that is provided separate from the article, and is selectively positioned in an operative proximity to the article. Desirably, the interrogator can be provided by a component that is selectively positioned or positionable in a cooperative proximity to the transponder 28.

In a particular aspect, the input energy can be of radio-frequency (RF) and the radio-frequency can be at least a minimum of about 0.1 MHz. The radio-frequency can alternatively be at least about 5 MHz, and optionally, can be at least about 7 MHz to provide improved performance. In other aspects, the radio-frequency can be not more than a maximum of about 50 MHz. The radio-frequency can alternatively be not more than about 15 MHz, and optionally, can be not more than about 12 MHz to provide improved effectiveness.

The desired selection of the input frequency can provide particular advantages. For example, the higher frequencies can allow the use of smaller electronic components. The lower frequencies can reduce the amount of power needed to generate the desired input energy.

The transponder 28 can be configured to return a portion of the input energy to the interrogator 30 and thereby communicate the indicator data away from the article 20. In particular aspects, the transponder can be configured to employ a sonic, optical and/or electromagnetic technique or device to return the desired portion of the input energy to the interrogator 30. In a desired aspect, the transponder 28 can be configured to electronically return a portion of the input energy to the interrogator.

In the example representatively shown in FIGS. 1, 4, 5A and 6, the interrogator 30 can include an interrogator coil 52. Additionally, the transponder 28 can include an operative transponder coil 50. The transponder coil 50 has an inductive impedance. Similarly, the interrogator coil 52 has an inductive impedance. In particular configurations, the passive transponder 28 can respond through an electronic coupling which can, for example, include an inductive coupling between the transponder coil 50 and the interrogator coil 52. In the various configurations of the invention, the interrogator coil 52 can be interpreted as being an antenna.

The technique of the invention can include a positioning of the interrogator coil 52 in an operative proximity to the transponder coil 50. In a desired aspect, the interrogator coil can be positioned in a substantially coaxial relation with the transponder coil 50, and the central axis of the interrogator coil can be aligned to substantially coincide with the central axis of the transponder coil. The input energy is delivered to the interrogator coil 52, and the input energy is operatively transmitted from the interrogator coil 52 to the transponder coil 50. A quantity of output energy which carries indicator data is received by the interrogator coil 52. In particular aspects, the interrogator coil 52 can receive output energy which is reflected back into the interrogator coil 52 from the transponder coil 50. A threshold value of the indicator data is operatively detected, and a presence of the threshold value of the indicator data is operatively signaled. In the various arrangements of the invention, the signaling or announcing of the threshold value can employ any operative display mechanism or technique.

In the representatively shown arrangement, the transponder coil 50 can be a single or multiple turn coil having a selected diameter 54 (e.g. FIG. 5). Additionally, the interrogator coil 52 may also be a single or multiple turn coil having a selected diameter 56 (e.g. FIG. 5A). The diameter 54 of the transponder coil and the diameter 56 of the interrogator coil can have a selected ratio. The selected ratio can be configured to increase the coupling coefficient, k, between the transponder coil 50 and the interrogator coil 52. The increased coupling coefficient can increase the efficiency of the transfer of energy between the coils. A desired coil diameter of one of the two coils is selected based upon the physical constraints of the article 20 and the wavelength/frequency of the energy intended for operation. In the shown arrangement, for example, it is convenient to initially select the size of the transponder coil, based on the space-available and the ease of positioning the transponder coil in the article.

The diameter of the second coil can then be found to increase the coupling coefficient, k. In particular aspects, the diameter of the second coil can be based upon the diameter of the first coil, and the expected separation distance between the two coils. For example, see F. E. Terman, *Radio Engineer's Handbook*, first edition, McGraw-Hill Book Company, Inc. New York, 1943, e.g. pages 67–73. In the shown configurations, the separation distance is primarily determined by the total thickness of the various layers of material (e.g. layers of the article 20 and the system package module 68) that are interposed between the transponder coil 50 and interrogator coil 52 during ordinary operation. When the first and second coils (e.g. the transponder coil and interrogator coil) are positioned in a spaced-apart, substantially coaxial relation, it can be determined that an increased or maximized coupling coefficient, k, can be provided when the coil diameters are configured in accordance with the following formula:

$$d_1 = ((d_2)^2 + 4D^2)^{1/2}$$

where:
$d_2$=diameter of the relatively smaller coil
$d_1$=diameter of the relatively larger coil
D=separation distance between the two coils In desired arrangements, where the separation distance, D, can be expected to be about 5 mm±1.5 mm, the diameter 56 of the interrogator coil 52 is approximately 1.25 times the diameter 54 of the transponder coil 50 to provide improved performance. In the representatively shown configuration, for example, the interrogator coil can have a diameter of about 1.25 inches (about 3.2 cm), and the transponder coil 50 can have a diameter 54 of about 1 inch (2.54 cm).

With reference to FIGS. 1, 3A, 4 and 5, the transponder 28 can include an electronically tuned circuit which can electronically resonate at the predetermined input frequency, or substantially at the input frequency. Similarly, the interrogator 30 can include an electronically-tuned resonant circuit which is tuned to electronically resonate at the selected input frequency, or substantially at the input frequency. For example, the interrogator may be tuned with an appropriately sized tuning capacitor 46. Where the interrogator 30 employs RF power at a 10 MHz input frequency and a 1 inch diameter, single-turn transponder coil 50, the interrogator can be tuned with a parallel connected, 3900 pF capacitor.

In another aspect, the output receiver 34 can include a circuit that can electronically resonate at the predetermined input frequency. In a further aspect, the transponder 28 can be configured to deliver the desired output energy at a predetermined output frequency. In desired arrangements, the output frequency can substantially equal the input frequency. In alternative arrangements the output frequency may differ from the input frequency.

A primary energy source 58 is operatively configured to provide the input energy. In desired arrangements, the primary energy source is separately provided and is electrically isolated from the article 20. The desired electrical isolation can be provided by the wireless communication between the passive transponder 28, and the interrogator 30 and output receiver 34.

Figure 4:
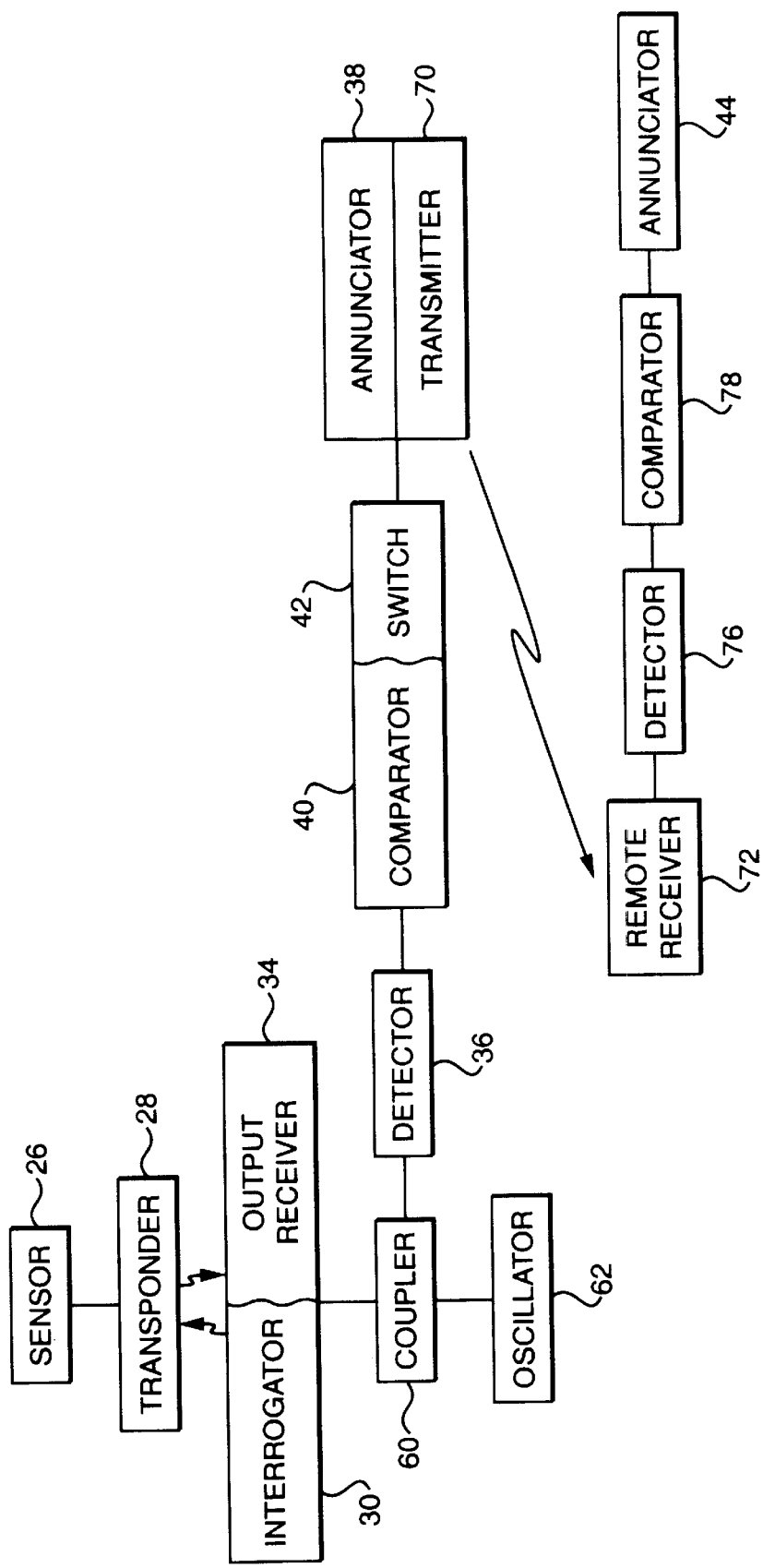
FIG. 4 representatively shows a schematic block diagram of the apparatus and method of the invention.
Figure 6A:
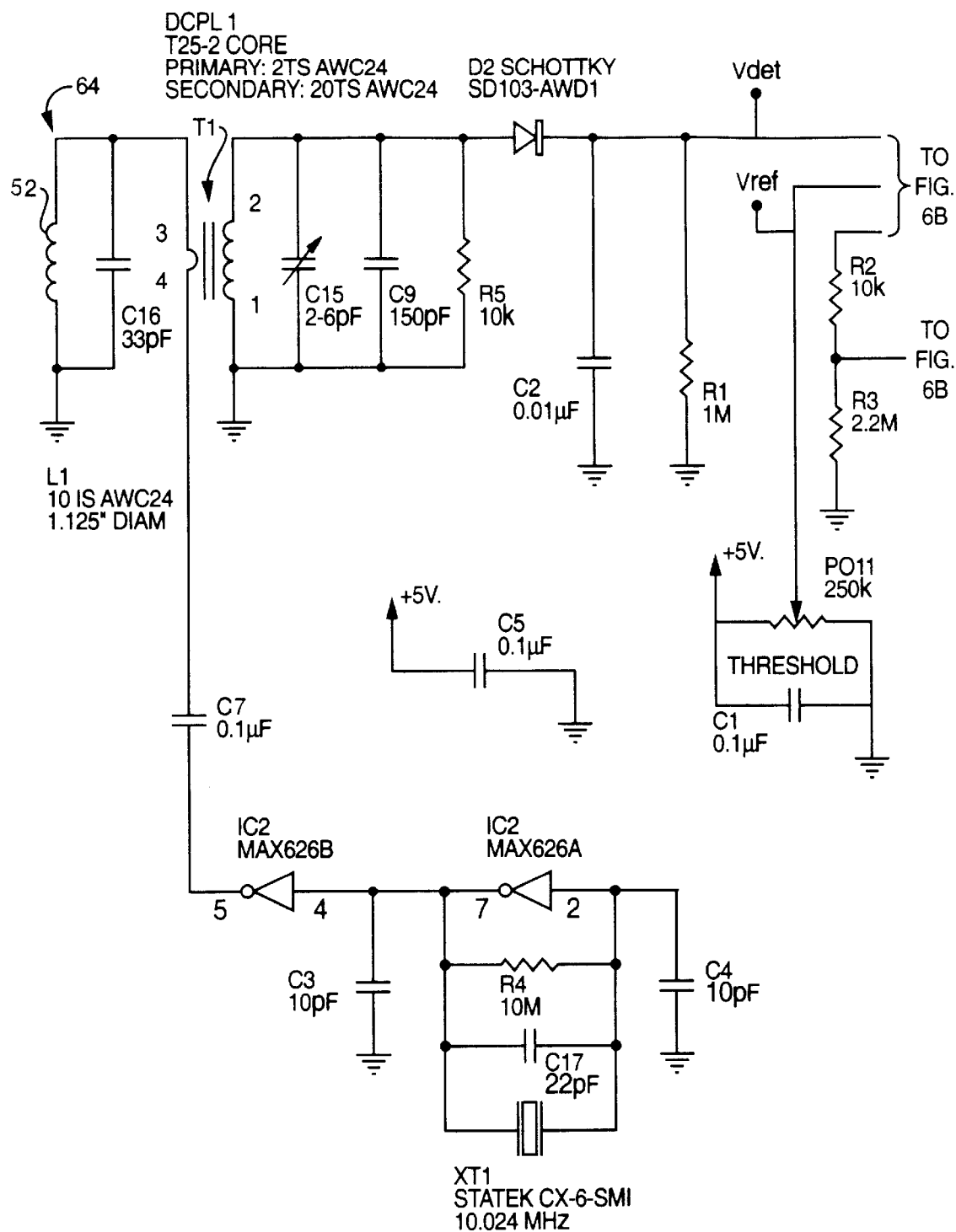
FIG. 6A and FIG. 6B collectively) representatively shows a schematic circuit diagram of an electronic package module that can be employed with the present invention.
Figure 6B:
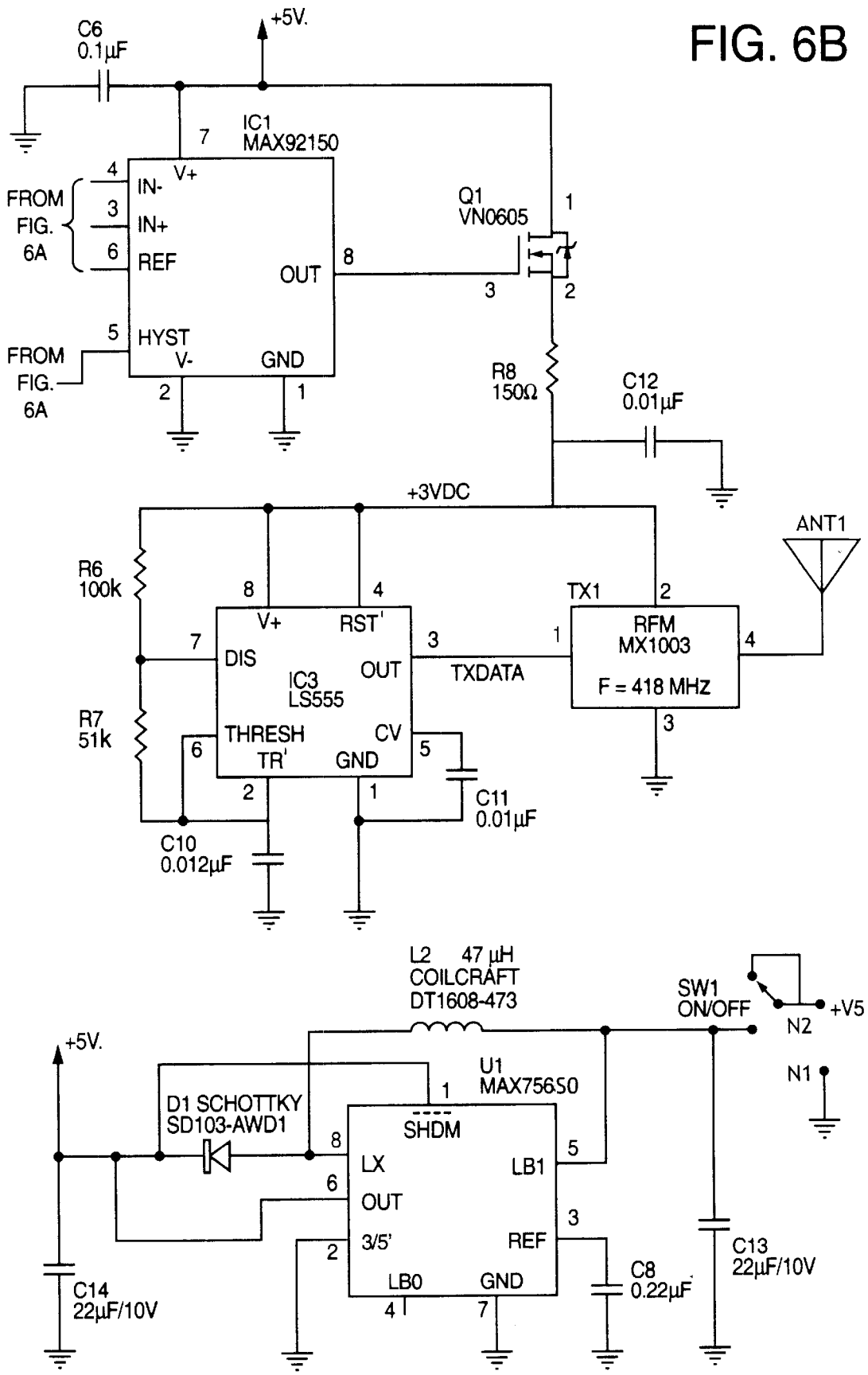

With ref to FIGS. 4, 5 and 6, a particular aspect of the invention can include a configuring of an output receiver 34 to electronically acquire the appointed indicator data communicated from the transponder 28. In particular arrangements, the output receiver can have the configuration of an electronic, directional coupler 60. A detector 36 is connected to resolve the indicator data from energy that is delivered from the output receiver 34. For example, the delivered level of energy can vary in an amount that corresponds to the selected first and second condition of the monitored portion 22. In a particular aspect, an electronic sampler can be employed to monitor a value provided by or derived from the indicator data. For example, a comparator 40 can be configured to react to a threshold value of the indicator data. An annunciator is operatively connected in communication with the detector 36, and is configured to announce a presence of at least the threshold value of the indicator data. The mechanism and technique for providing the connected communication may, for example, include a switch 42

The annunciator 38 can be configured to provide any suitable, desired display. For example, the annunciator 38 may be configured to provide an audio display. Alternatively, the annunciator may be configured to provide a visual display. Optionally, the annunciator can provide another type of display, such as a tactile display, a vibratory display, an olfactory display or the like, as well as combinations thereof.

In another aspect, the annunciator 38 can be configured to include a pager or other relaying device which can operatively communicate the desired assessment of the indicator data and/or the recognized presence of the threshold value to a more remote location. Such information can, for example, be communicated in the form of selected signal data. With reference to FIGS. 4, 5A, 6, 7 and 8, the relay device can include a supplemental transmitter 70 which can operatively send the desired signal data, and a supplemental receiver 72 which can operatively receive the relayed signal data delivered from the supplemental transmitter. The supplemental transmitter can be an infrared transmitter, an ultrasonic transmitter an RF transmitter or the like, as well as combinations thereof. Accordingly, the corresponding and cooperating receiver can be an infrared receiver, an ultrasonic receiver, a RF receiver or the like, as well as combinations thereof. In the representatively shown example, the supplemental transmitter can be a radio-frequency transmitter, and the supplemental receiver can be a radio-frequency receiver. Additionally, the relay device can include a remote annunciator display which announces the presence of the threshold value of the indicator data. As mentioned elsewhere herein, the annunciator display can be provided by any suitable display mechanism or technique, as desired.

A desired configuration of a method and apparatus for remotely indicating a dry or wet condition in a non-metallic material or substrate can include a wireless RF link produced at the selected input frequency. The link can be made between an external RF source and a passive (i.e. no power source) tuned circuit portion that is embedded in a non-metallic article, such as a diaper, or other garment (e.g. FIGS. 1, 3 and 3A). The RF link can be implemented by employing a stable RF source and the companion, resonant tuned circuit which is embedded in the article and electronically coupled to the RF source employing the interrogator 30. The power supply for the circuits of the external portion of the apparatus may be provided by commonly available batteries, such as an AAA-size battery cell or a coin cell. When the monitored portion 22 of the article is wetted with an electrically conductive liquid, such as urine, the wet condition can be sensed by detecting electrical resistance changes that arise in the wetted sections of article. The external portion can send another RF signal at a selected, second RF frequency to a remotely located paging unit to remotely signal the detected, wetted condition.

The power supply and associated circuitry of the desired external portion of the signaling device can be housed in a suitable system package module 68. In desired configurations, the system module 68 is distinctively compact and lightweight. For example, the system module 68 can have a weight of not more than about 15 grams. Additionally, the system module 68 can have dimensions which are less than about 4 centimeters in width, less than 4 centimeters in height, and less than 1 centimeter in depth or thickness.

The package module 68 can also include an operative mounting device for securing the system module 68 onto the selected target article 20. Various types of conventional mechanisms can be employed to hold the package module 68 on the target article. Such holding mechanisms can, for example, include adhesives, snaps, hooks, inter-engaging mechanical fasteners, hook-and-loop fasteners, magnetic fasteners or the like, as well as combinations thereof. In the illustrated configuration, for example, the system package module 68 can include a hook component and the target zone of the article 20 can include a complementary loop material.

The system can employ a two-way wireless radio link between an external micro-power RF source and the passive transponder 28 that is embedded in the non-metallic substrate of the selected article. A micro-power RF carrier is transmitted from a small (about 3.2 cm) external antenna coil, such as provided by the interrogator coil 52. In the shown arrangement, a substantially steady RF carrier can be transmitted. Alternatively, the transmission of the RF carrier can be non-steady. For example, the configuration of the transmitted RF can be timed, cycled on-off or otherwise varied. The external antenna coil can be closely magnetically coupled to a smaller (about 2.5 cm), internal antenna coil, such as provided by the transponder coil 50. The internal coil is desirably embedded in the monitored portion of the absorbent pad. These coils can be interpreted as constituting a transformer coupling between the tuned primary circuit with its external coil, and the tuned secondary circuit with its embedded coil. The diameter difference in the primary and secondary coils permits some tolerance to expected misalignments and relative motions between the coils. When the primary and secondary circuits are operatively coupled, a portion of the energy coupled from the primary circuit to the secondary circuit is reflected back from the secondary circuit and appears in the primary circuit. The amount of energy reflected into the primary circuit is related to the impedance that appears across the secondary circuit. In the representatively shown arrangement, the secondary circuit includes a resistance-type sensor.

The illustrated sensor can, for example, be composed of two small gauge wires (e.g.: #24 AWG) spaced about 1 cm apart and located in the absorbent of the representatively shown diaper article. The electrical resistance across these wires will be large (open-circuit or high-resistance) when the monitored portion of the diaper is dry, and much smaller when the monitored portion of the diaper is wetted with an electrically conductive material such as urine. The spaced-apart ends of these wires are electrically connected in parallel with the secondary tuned circuit. As a result, the dry absorbent pad can provide a reflected signal, into the external primary circuit, that is significantly different from the reflected signal provided by a wetted absorbent pad.

To provide the desired input energy, the energy source can be a micro-power system using a quartz crystal referenced oscillator, oscillating at the selected input frequency, and power amplifier. The amplifier output is directly connected to the series tuned primary circuit composed of the external coil and an adjustable, resonating capacitor. Located between the power amplifier and the primary circuit is a directional coupler 60 from which the energy reflected from the coupled secondary circuit can be sampled and monitored. The directional coupler may be any device that can operatively separate the forward signal (from the power amplifier) from the reflected signal that is returned into the primary circuit from the secondary circuit located in the article. The reflected output from the directional coupler is next detected to provide a voltage Vdet the magnitude of which is related to the amplitude of the reflected energy, and therefore, related to the magnitude of the resistance across the sensor. This voltage is significantly different for a dry absorbent pad as compared with a wetted absorbent pad.

With reference to FIGS. 4, 5A and 6, the input frequency can be provided by any conventional generating device. For example, the representatively shown arrangement can employ a crystal controlled oscillator 62 which generates the input energy at a frequency of about 10.024 MHz. The radio-frequency power is suitably amplified and buffered, such as by employing circuitry which includes the shown IC2 (e.g. MAX 626A device, available from Maxim Semiconductor, a business located in Sunnyvale, Calif.). The RF power is delivered to the interrogator antenna circuit 64, and the antenna can, for example, be provided by the interrogator coil 52.

A directional coupler 60 can be provided by various types of operative circuits that are well known in the art. For example, in the representatively shown configuration, the directional coupler can be provided by the circuitry that includes the shown transformer T1, and associated capacitors C15 and C9, along with resistor R5. As illustrated, capacitor C15 can be adjusted to tune a reception of the output energy received by the interrogator coil 52 from the transponder coil 50. A suitable sampler can monitor a value that is provided by or derived from the indicator data delivered from the directional coupler. In the representatively shown configuration, the sample can employ a detector to deliver a selected signal for further processing. For example, the representatively shown arrangement can include an envelope detector. The detected signal voltage Vdet can then be delivered to a conventional comparator device.

Various conventional detection schemes can be employed. For example, the detected voltage can be high or low when the monitored portion 22 of the article 20 is in its first (e.g. dry) condition. Similarly, the detected voltage signal can be high or low when the monitored portion 22 of the article is in its second (e.g. wet) condition. In the representatively shown arrangement, the detection scheme is configured such that the detected voltage is high when the monitored portion is in its dry condition, and the detected voltage is low when the monitored portion of the article is in its wet condition.

The detector 36 can include an envelope detector, such as provided by the representatively shown circuitry that includes capacitor C2, resistor R1 and diode D2 (e.g. Schottky SD103-AWDI device, available from Diodes, Inc., a business having offices located in Westlake Village, Calif.). The envelope detector can operatively detect the indicator data received from the directional coupler, and can employ the indicator data to generate the detected voltage Vdet.

As representatively shown, the method and apparatus of the invention can desirably include a voltage threshold detector system 40. The voltage threshold detector system can include a comparator, and a switch 42 that can open and close according to the amplitude of a voltage placed on its input. As representatively shown, the comparator can be provided by circuitry that includes IC1 (e.g. MAX 921 device, available from Maxim Semiconductor). The switching operation can be provided by circuitry that includes Q1.

In the example of the shown configuration, the voltage Vdet corresponding to a wetted absorbent can be configured to turn the switch ON, and the Vdet corresponding to a dry absorbent can be configured to turn the switch OFF. The switching threshold can desirably be adjustable to account for different applications or conditions, such as for different resistances of the monitored non-metallic substrate material and for different non-metallic substrate material thickness).

When the comparator or other component of an operative threshold detector 40 sees that the indicator data, as represented by the detected voltage Vdet, has reached a selected threshold value, the comparator can generate a predetermined output signal. In the shown configuration, the output signal from the comparator is generated when the detected voltage Vdet falls below a predetermined reference voltage Vref.

A desired reference voltage Vref can be provided by employing any conventional circuitry. For example, the shown arrangement can provide the reference voltage by employing a THRESHOLD circuitry which includes adjustable potentiometer POT1.

The output signal from the comparator can be configured to operate any conventional switching device or switching circuit. For example, the shown configuration of the switching circuit can employ a Q1 provided by a MOSFET (metal oxide semiconductor field effect transistor) device (e.g. VN0605 device available from Vishay Siliconix, a division of Vishay Intertechnology, Inc., a business having offices located in Malvern, Pa.). In the shown arrangement, the switch is normally open, and the switch becomes closed when the output signal from the comparator is received. The closing of the switch can be employed to activate a suitable annunciator system, and the annunciator can include any operative display. For example, the output delivered from the switching circuits can be configured to activate an audible beeper or other type of alarm that is contained in the external portion of the system, such as provided by the package module 68.

In a desired aspect, the annunciator can include a relaying or paging system or unit which can operatively deliver a relay signal to a more remote location. More particularly, the relaying device can be employed to announce the presence of the threshold value of the indicator data at the more remote location.

In the example of the representatively shown configuration, the relaying device can include a supplemental transmitter 70 which can have a RF transmitter and a cooperating signal generator. The transmitter can be provided by a conventional circuit, such as a circuit which includes an RF module which is configured to transmit at a frequency of 418 MHz. As representatively shown, the RF transmitter can be provided by circuitry which includes circuit module TX1 (e.g. HX1003 device, available from R. F. Monolithics, Inc., a business having offices located in Dallas, Tex.). The signal generator can employ any conventional circuitry such as a circuit which includes the representatively shown IC3 (e.g. LS555 device, available from National Semiconductor, Inc., a business having offices located in Santa Clara, Calif.). In the representative example of the shown arrangement, the signal generator produces a square wave at a frequency of about 1 KHz. The 1 KHz signal is employed to modulate the transmitted RF frequency and energy directed into and emitted by an operative antenna 104. In the shown arrangement, the radio frequency transmission is modulated by employing on-off keying. Other types of modulation may alternatively be employed. Such modulation may include phase shift keying, frequency shift keying, digital code modulation or the like, as well as combinations thereof. The various circuits of the input frequency generator, the directional coupler, the detector, the comparator, and the annunciator system can be powered with a suitable module power supply. In the shown configuration, the power supply can include a conventional battery, such as a 1.5 volt battery cell. The power supply can also employ a boost voltage switching converter, such as a voltage switching converter which includes the representatively shown circuit device U1 (e.g. MAX756 device, available from Maxim Semiconductor, Inc.).

Figure 7:
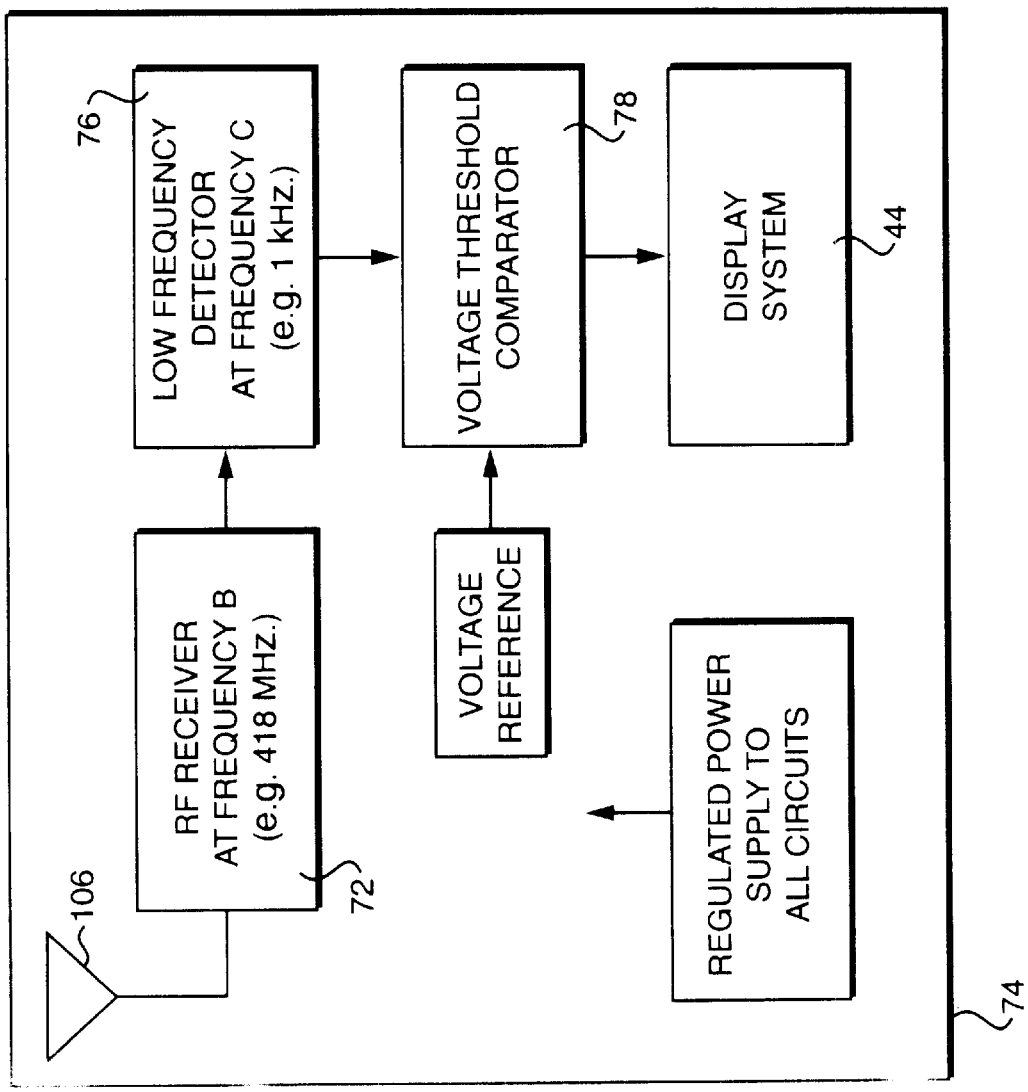
FIG. 7 representatively shows a schematic block diagram of remote paging unit that can be employed with the present invention FIG. 8 (i.e.
Figure 8A:
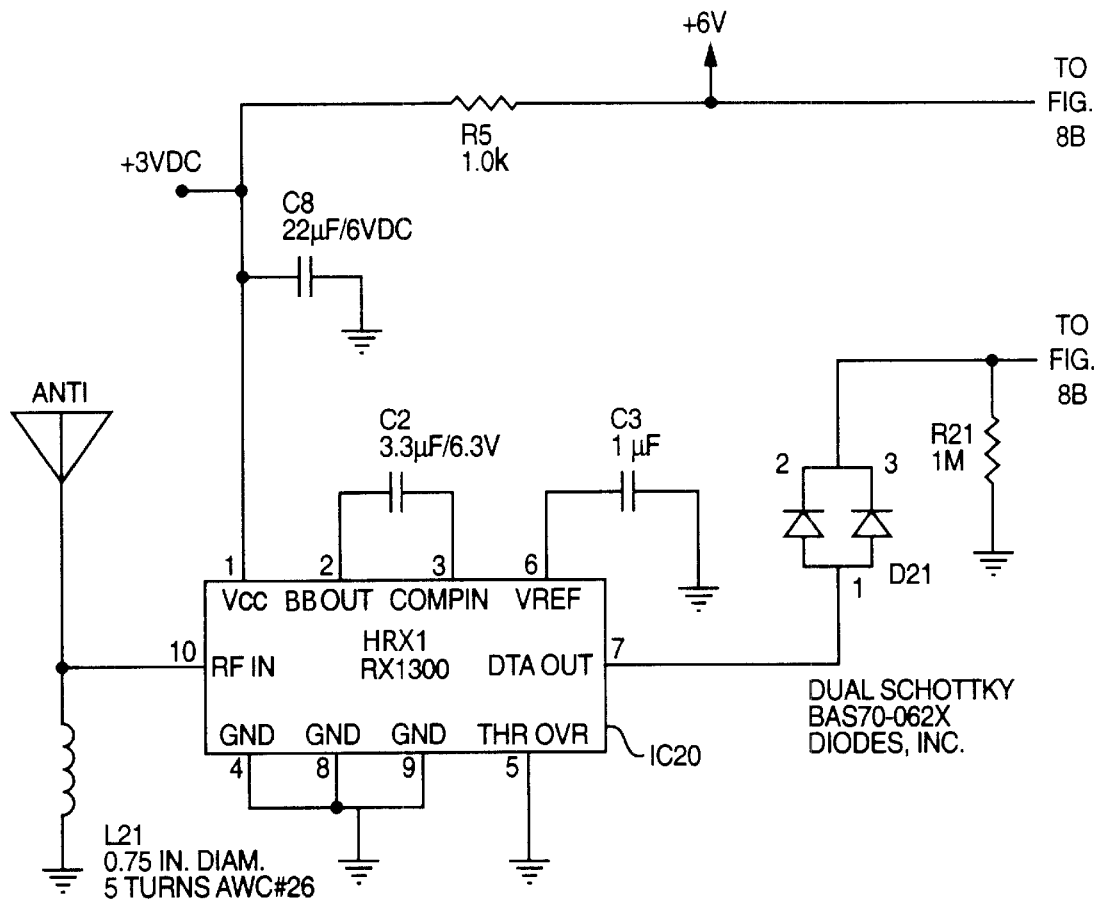
FIG. 8A and FIG. 8B collectively) representatively shows a schematic circuit diagram of a remote paging unit that can be employed with the present invention.
Figure 8B:
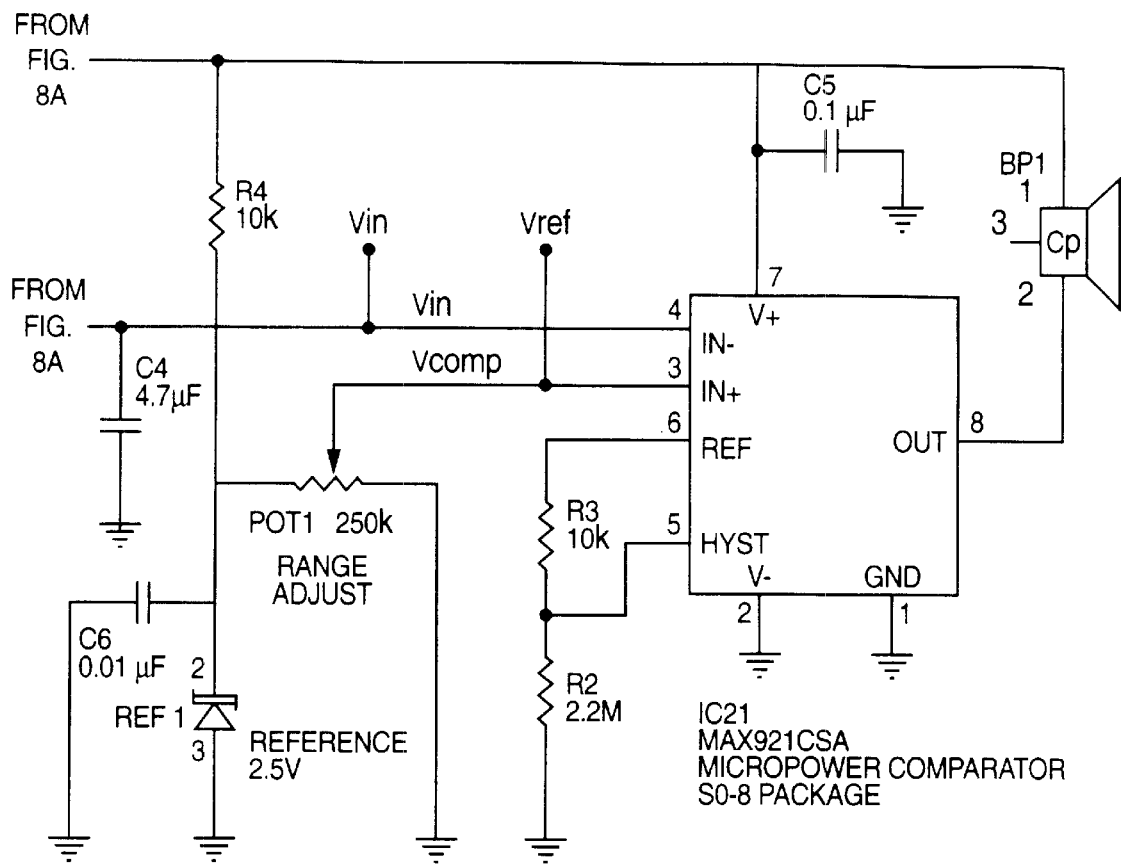
Figure 8B:
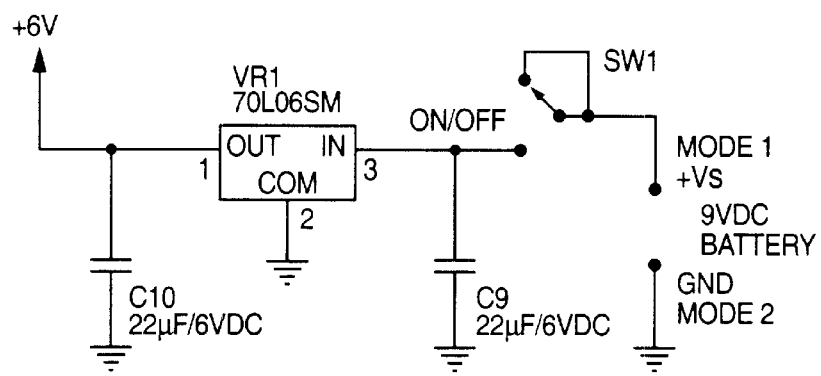

With reference to FIGS. 4, 7 and 8, the relaying system can include a separately provided, remote paging unit 74. The paging unit can include a suitable supplemental receiver 72 which, in the shown arrangement, can be a cooperating RF receiver. The paging unit can further include, a signal detector 76, a comparator 78 or other threshold detector and a suitable display system, such as provided by a remote annunciator 44, along with an associated power supply. The receiver portion of the paging unit is configured to receive the transmission generated by the relaying device on the system module 68. Any conventional, compatible receiving circuitry can be employed.

As representatively shown, the remote receiving system may include a single-chip hybrid AM radio receiver having a receiving antenna 106, a low frequency detector 76, a voltage level comparator, an alarm annunciator (such as an audible beeper), and a voltage regulated power supply (e.g. FIGS. 7 and 8). The RF signal (e.g. at 418 MHz.) can be received using the amplitude modulation receiver hybrid chip. The output from the receiver 72 can be a constant amplitude square wave at the selected modulation frequency (e.g. 1 KHz). This low frequency square wave signal can subsequently be detected to provide a voltage whose amplitude is related to the strength of the received RF signal, thereby providing a method and apparatus for activating the remote receiving system by an out-of-operating-range situation. This voltage is compared with an adjustable reference voltage with the comparator circuit that follows. Thus, a wetted absorbent (or an out-of-range situation) will result in activation of the selected annunciator or alarm device (e.g. audible beeper).

The receiving circuitry can, for example, employ an integrated circuit module IC20. An example of a suitable integrated circuit HRX1 is an RX1300 device available from R.F. Monolithics, Inc. The modulated signal on the received radio frequency is operatively detected. The detector can employ any suitable, conventional circuitry. In the shown arrangement, the detector is provided by circuitry which includes resistor R21, capacitor C4 and a system of diodes D21 (e.g. Dual Schottky BAS70-062X device, available from Diodes, Inc.). The detected signal can be employed to generate a detected voltage Vin, and the detected voltage can be delivered to a suitable comparator circuit. The comparator circuit can, for example, include the representatively shown IC21 (e.g. MAX921 micro-power comparator). The detected voltage Vin is compared to a reference voltage Vref when the detected voltage Vin reaches a selected value the comparator can generate an output signal which activates a suitable display unit. In the example of the shown arrangement, the display unit includes an audio beeper BP1.

The paging unit includes a suitable power supply such as a power supply which includes a battery. In the shown arrangement the power supply employs a nine volt battery which is connected to a voltage regulator VR1 (e.g. 78L06SM device, available from National Semiconductor, Inc.) which provides a desired regulated voltage. In the shown arrangement, the voltage is regulated to a value of about 6 volts.

When arranged for use, the passive transponder 28 can be located at any convenient position in the selected article 20. The transponder or an operative portion thereof may be located a front, back or side location of the article, as desired. For example, the transponder coil 50 may be located at a predetermined position along a waistband portion of a diaper, as representatively shown in FIG. 1 through 3A. In a desired arrangement, the transponder coil may be positioned at a generally centered location at the front waistband section of the diaper. Electrically conductive, insulated wires can operatively connect the transponder (e.g. the portion provided by transponder coil 50) to the sensor 26. In a desired configuration, the sensor can be provided by bare ends (insulation removed) of the connecting wires which can be spaced-apart by an operative distance. For example, bare wire ends can be spaced apart by a distance of about 1 cm. The sensor (e.g. bare wire ends) can be located at any operative position in the article. In an example of a desired arrangement, the sensor can be positioned in an appointed front section of the diaper proximate an intermediate, crotch portion of the absorbent pad.

An operative portion of the transponder (e.g. transponder coil 50) can be positioned proximate any operative surface of the article, which may be a top surface, bottom surface, side surface, inward surface or outward surface, as desired. For example, the transponder coil can be positioned in an operative location that is proximately adjacent an appointed outward surface of the diaper. Additionally, the plane of the coil can desirably be aligned generally parallel to the outward surface of the diaper.

During ordinary use, the interrogator can be positioned in an operative proximity to the passive transponder 28. For example, the interrogator coil 52 can be located adjacent an outward surface of the package module 68 with the plane of the interrogator coil arranged generally parallel to the outward surface. The package module can be secured to the diaper with a suitable, fastener to operatively align the interrogator coil 52 with the transponder coil 50. Desirably, the fastener is capable of being selectively removable and refastenable (e.g. a hook-and-loop fastener). In a desired configuration, the transponder coil and interrogator coil can be approximately, concentrically arranged. Even though there are intervening layers of the article (e.g. the diaper outer cover), there can be an operative, wire-less communication between the transponder coil and the interrogator coil. In the example, of the representatively shown configuration, the selected annunciator (e.g. the paging unit 74) can be configured to activate its associated display (e.g. "beep") until an operative positioning is established between the interrogator and transponder (e.g. an operative alignment between the interrogator coil 52 and the transponder coil 50).

Having described the invention in rather full detail, it will be readily apparent that various changes and modifications can be made without departing from the scope of the invention. All of such changes and modifications are contemplated as being within the scope of the invention as defined by the subjoined claims.

We claim:

1. A monitoring system for signaling a predetermined status in an article, said monitoring system comprising:
   an interrogator which is located in an operative proximity to said article, and is configured to provide input energy with a predetermined input frequency;
   a status signaling device located in a monitored portion of said article; said status signaling device including
      a sensor which can indicate a change of state that occurs when said monitored portion of said article changes from a first condition to a different, second condition, said sensor indicating said change of state by providing a change of electronic impedance that occurs when said monitored portion changes from said first condition to said second condition; and
      a passive transponder which is in an operative communication with said sensor,
      said transponder configured to receive said input energy from said interrogator,
      said transponder configured to generate indicator data when said monitored portion is in said second condition,
      said indicator data including a change in an amount of energy reflected through said transponder, such change in reflected energy provided by the change of electronic impedance that occurs when said monitored portion changes from said first condition to said second condition, and
      said transponder configured to communicate an output energy away from said article, said output energy including at least a portion of said input energy, and said output energy configured to carry said indicator data;
   an output receiver that is configured to electronically acquire said output energy and indicator data from said transponder;
   a detector which is connected to said output receiver and can react to a threshold value of the amount of energy reflected through said transponder in said indicator data; and
   an annunciator which is in communication with said detector and is configured to announce a presence of said threshold value of said amount of energy reflected through said transponder.

2. A monitoring system as recited in claim 1, wherein said article includes an absorbent body having said monitored portion;
   said sensor which can indicate said change in state by providing a change of electronic impedance that occurs when said monitored portion of said absorbent body changes from a substantially dry, first condition to a wetted, second condition; and
   said passive electronic transponder is configured to generate said indicator data when said absorbent body is in said wetted, second condition.

3. A system as recited in claim 2, wherein said output receiver includes an electronic sampler which monitors a value provided by said indicator data.

4. A system as recited in claim 2, wherein said monitoring system further includes:
   a supplemental radio-frequency transmitter;
   a supplemental radio-frequency receiver which can receive relayed data delivered from said supplemental transmitter; and
   a remote display which can announce said presence of said threshold value of said indicator data.

5. A system as recited in claim 4, wherein said remote display includes an audio display.

6. A system as recited in claim 4, wherein said remote display includes a visual display.

7. A system as recited in claim 4, wherein said remote display includes a tactile display.

8. A method for signaling a predetermined status in an article, said method comprising:
   a locating of an interrogator in an operative proximity to said article, and is configured to provide input energy with a predetermined input frequency;
   a locating of a status signaling device in a monitored portion of said article; said status signaling device including
      a sensor which can indicate a change of state that occurs when said monitored portion of said article changes from a first condition to a different, second condition, said sensor indicating said change of state by providing a change of electronic impedance that occurs when said monitored portion changes from said first condition to said second condition; and
      a passive transponder which is in an operative communication with said sensor,
      said transponder configured to receive said input energy from said interrogator,
      said transponder configured to generate indicator data when said monitored portion is in said second condition,
      said indicator data including a change in an amount of energy reflected through said transponder, such change in reflected energy provided by the change of electronic impedance that occurs when said monitored portion changes from said first condition to said second condition, and
      said transponder configured to communicate an output energy away from said article, said output energy including at least a portion of said input energy, and said output energy configured to carry said indicator data;
   a configuring of an output receiver to electronically acquire said output energy and indicator data from said transponder;
   a connecting of a detector to said output receiver to react to a threshold value of the amount of energy reflected through said transponder in said indicator data; and
   a configuring of an annunciator which is in communication with said detector to announce a presence of said threshold value of said amount of energy reflected through said transponder.

9. A monitoring system for signaling a predetermined status in an article, said monitoring system comprising:
   an interrogator coil which is located in an operative proximity to said article, and is configured to provide input energy with a predetermined input frequency;
   a status signaling device located in a monitored portion of said article; said status signaling device including
      a sensor which can indicate a change of state that occurs when said monitored portion of said article changes from a first condition to a different, second condition, said sensor indicating said change of state by providing a change of electronic impedance that occurs when said monitored portion changes from said first condition to said second condition; and
      a passive transponder which is in an operative communication with said sensor;
      said transponder configured to receive said input energy from said interrogator, said transponder configured to generate indicator data when said monitored portion is in said second condition, said transponder including a transponder coil having an inductive impedance;

said transponder coil and a capacitor being configured to provide an electronically-tuned resonant circuit which is operatively tuned to said input frequency, said indicator data including a change in an amount of energy reflected to said interrogator coil through said transponder coil, such change in reflected energy provided by the change of electronic impedance that occurs when said monitored portion changes from said first condition to said second condition, and said transponder configured to communicate an output energy away from said article, said output energy including at least a portion of said input energy, and said output energy configured to carry said indicator data;

an output receiver that is configured to electronically acquire said output energy and indicator data from said transponder;

a detector which is connected to said output receiver and can react to a threshold value of the amount of energy reflected through said transponder coil; and an annunciator which is in communication with said detector and is configured to announce a presence of said threshold value of said amount of energy reflected through said transponder.

10. A method for signaling a predetermined status in an article, said method comprising:

a locating of an interrogator coil in an operative proximity to said article, and is configured to provide input energy with a predetermined input frequency;

a locating of a status signaling device in a monitored portion of said article; said status signaling device including a sensor which can indicate a change of state that occurs when said monitored portion of said article changes from a first condition to a different, second condition, said sensor indicating said change of state by providing a change of electronic impedance that occurs when said monitored portion changes from said first condition to said second condition; and a passive transponder which is in an operative communication with said sensor, said transponder configured to receive said input energy from said interrogator, said transponder configured to generate indicator data when said monitored portion is in said second condition, said transponder including a transponder coil having an inductive impedance;

said indicator data including a change in an amount of energy reflected to said interrogator coil through said transponder coil, such change in reflected energy provided by the change in electronic impedance that occurs when said monitored portion changes from said first condition to said second condition, and said transponder configured to communicate an output energy away from said article, said output energy including at least a portion of said input energy, and said output energy configured to carry said indicator data;

a configuring of an output receiver to electronically acquire said output energy and indicator data from said transponder;

a connecting of a detector to said output receiver to react to a threshold value of the amount of energy reflected through said transponder; and a configuring of an annunciator which is in communication with said detector to announce a presence of said threshold value of said amount of energy reflected through said transponder.

\* \* \* \* \*